US011034886B2

(12) United States Patent
Bryan et al.

(10) Patent No.: US 11,034,886 B2
(45) Date of Patent: Jun. 15, 2021

(54) METHOD FOR VISUALLY ENHANCING THE EXPERIENCE OF AN AUDIENCE DURING A PERFORMANCE

(71) Applicant: PROLUME, LTD., Pinetop, AZ (US)

(72) Inventors: Bruce Bryan, Beverly Hills, CA (US); Hendrik Schmidt, Denver, CO (US); Millard Cull, Brighton, CO (US)

(73) Assignee: Prolume, LTD., Pinetop, AZ (US)

( * ) Notice: Subject to any disclaimer, the term of this patent is extended or adjusted under 35 U.S.C. 154(b) by 0 days.

(21) Appl. No.: 16/378,541

(22) Filed: Apr. 8, 2019

(65) Prior Publication Data

US 2019/0233722 A1   Aug. 1, 2019

Related U.S. Application Data

(60) Division of application No. 15/490,714, filed on Apr. 18, 2017, now Pat. No. 10,253,254, which is a continuation of application No. 14/424,969, filed as application No. PCT/US2013/057660 on Aug. 30, 2013, now Pat. No. 9,624,425.

(60) Provisional application No. 61/696,136, filed on Sep. 1, 2012.

(51) Int. Cl.
| | |
|---|---|
| *C07D 487/22* | (2006.01) |
| *C09K 11/07* | (2006.01) |
| *C12N 9/02* | (2006.01) |
| *A61K 38/17* | (2006.01) |
| *A61K 38/44* | (2006.01) |
| *A63J 5/02* | (2006.01) |
| *C07D 487/04* | (2006.01) |
| *A61K 49/00* | (2006.01) |

(52) U.S. Cl.
CPC .......... *C09K 11/07* (2013.01); *A61K 38/1767* (2013.01); *A61K 38/44* (2013.01); *A61K 49/0045* (2013.01); *A63J 5/02* (2013.01); *C07D 487/04* (2013.01); *C12N 9/0069* (2013.01); *C12Y 113/12007* (2013.01); *C09K 2211/1007* (2013.01); *C09K 2211/1018* (2013.01); *C09K 2211/14* (2013.01)

(58) Field of Classification Search
CPC .................................................. C07D 487/22
USPC ........................................................ 544/343
See application file for complete search history.

(56) References Cited

U.S. PATENT DOCUMENTS

| | | | |
|---|---|---|---|
| 6,232,107 | B1 | 5/2001 | Bryan et al. |
| 6,436,682 | B1 | 8/2002 | Bryan et al. |
| 6,458,547 | B1 | 10/2002 | Bryan et al. |
| 7,718,389 | B2 | 5/2010 | Ohmiya et al. |
| 9,624,425 | B2 | 4/2017 | Bryan et al. |
| 10,253,254 | B2 | 4/2019 | Bryan et al. |
| 2002/0090659 | A1 | 7/2002 | Bryan |
| 2006/0053505 | A1 | 3/2006 | Bryan |
| 2006/0234324 | A1* | 10/2006 | Inouye ............... A61K 49/0013 435/8 |
| 2010/0240146 | A1 | 9/2010 | Sommer-Knudsen et al. |
| 2011/0070656 | A1 | 3/2011 | Inouye |
| 2011/0081661 | A1 | 4/2011 | Armstrong et al. |
| 2011/0130704 | A1 | 6/2011 | Baldo et al. |
| 2011/0256564 | A1 | 10/2011 | Lune |
| 2012/0035070 | A1 | 2/2012 | Inouye et al. |
| 2012/0083012 | A1 | 4/2012 | Chang et al. |
| 2012/0232272 | A1 | 9/2012 | Inouye et al. |
| 2015/0225642 | A1 | 8/2015 | Bryan et al. |
| 2017/0217969 | A1 | 8/2017 | Bryan et al. |

FOREIGN PATENT DOCUMENTS

| | | |
|---|---|---|
| EP | 1925320 | 5/2008 |
| EP | 2893327 | 7/2015 |
| WO | 2014/036482 | 3/2014 |

OTHER PUBLICATIONS

Dorwald, Side Reactions in Organic Synthesis: A Guide to Successful Synthesis Design, Weinheim: Wiley-VCH, Verlag GmbH & Co. KGaA, 2005, Preface.
Supplemental EP Search Report for Application 13828899.8, dated Apr. 1, 2016, 7 pages.
EP Search Report for Application No. 13828899.8, dated Jul. 20, 2016, 15 pages.
First Examination report for Application 13828899.8, dated Mar. 6, 2019, 24 pages.
Inouye et al., "The Use of Renilla Luciferase, Oplophorus Luciferase, and Apoaequorin as Bioluminescent Reporter Protein in the Presence of Coelenterazine Analogues as Substrate", Biochemical and Biophysical Research Communications, 233, 349-353 (1997) Article No. RC976452.
International Preliminary Report on Patentability for PCT/US2013/057660, dated Mar. 3, 2015, 10 pages.
International Search Report for PCT/US2013/057660, dated Feb. 7, 2014, 33 pages.
Ohmiya et al., "Bioluminescence Activity of Coelenterazine Analogues after Incorporation into Recombinant Apoaequorin", Chemistry Letters, pp. 2149-2152, 1993.

(Continued)

*Primary Examiner* — Douglas M Willis
(74) *Attorney, Agent, or Firm* — Adsero IP

(57) ABSTRACT

Novel compounds in the classes of Imidazo[1,2-α]pyrazines and Imidazo[1,2-α]quinoxalines with a methoxy group modification show unique spectral properties when used as a substrate for luciferases and photo-proteins. Methoxy e-Coelenterazine, an Imidazo[1,2-α] quinoxaline shifts the emission wavelength by 80 nm to blue light compared to e-Coelenterazine, using *Renilla reniformis* luciferase. The novel analogues described here are useful in combination with fluorescent proteins to create BRET (bioluminescent resonance energy transfer) and for other luminescent assays. In addition these novel compounds can be used to enhance, dazzle, amaze, startle, and otherwise entertain an audience by their direct application on to the audience, surroundings, the actors, or sprayed on settings as in the newer 4D movies.

16 Claims, 17 Drawing Sheets

(56) References Cited

OTHER PUBLICATIONS

Shimomura et al., "Structure of the Light-Emitting Moiety of Aequorin", Biochemistry, vol. 11, No. 9, 1972.
Stepanyuk et al., "Structure based mechanishm of the $Ca^{2+}$-induced release of coelenterazine from the Renilla binding protein", Proteins 2009, 74:583-593.
Zhao et al., "Characterization of Coelenterazine Analogs for Measurements of Renilla Luciferase Activity in Live Cells and Living Animals", Molecular Imaging, Jan. 1, 2004, vol. 3, No. 1: 43-54.

* cited by examiner

METHOD FOR VISUALLY ENHANCING THE EXPERIENCE OF AN AUDIENCE DURING A PERFORMANCE

CROSS-REFERENCE TO RELATED APPLICATIONS

This application is a divisional of U.S. application Ser. No. 15/490,714, filed Apr. 18, 2017, which is a continuation of U.S. application Ser. No. 14/424,969, filed Feb. 27, 2015, now U.S. Pat. No. 9,624,425, issued on Apr. 18, 2017, entitled "Novel Coelenterazine Compounds and Methods of Use", which application is a 35 U.S.C. § 371 national phase application of PCT/US2013/057660 (WO 2014/036482) filed on Aug. 30, 2013, entitled "Novel Coelenterazine Compounds and Methods of Use", which application claims the priority benefit of U.S. Provisional Application No. 61/696,136, filed Sep. 1, 2012 and entitled "Novel Coelenterazine Compounds and Methods of Use", which is incorporated herein by reference in its entirety. Any disclaimer that may have occurred during the prosecution of the above-referenced applications is hereby expressly rescinded, and reconsideration of all relevant art is respectfully requested.

TECHNICAL FIELD

The present disclosure teaches new Coelenterazine analogs that significantly modify the color and activity of Coelenterazine utilizing luciferases, and calcium activated photoprotein light emission. The present disclosure also teaches uses for such compounds. Such uses include systems for producing visible light chemically stored within a protein dissolved in water designed to emit visible or ultraviolet light that would visually enhance (surprise, startle, dazzle, amaze, scare or otherwise entertain) the audience experience during a theatrical, cinematic, stage, or music performance created by the direct application to the audience via their clothes, hair, and the chairs, flooring materials, upholstery, and any adjacent surfaces containing calcium on that surface.

BACKGROUND

The marine environment contains many animals with minimal or poorly developed nervous systems. Many of these animals have evolved systems to emit light in response to stimulation by contact with other animals. The general mediators for this release of visible light are trans-cellular and intra-cellular calcium ion messengers.

Many marine animals use Calcium Activated Photoproteins (herein know as CAP or CAPs) that luminesce in response to a local increase in the calcium concentration allowing the calcium ion to interact with the protein. For purposes herein, the word "calcium" refers to aqueous calcium ions in their ionic$^{+2}$ state.

The increase in local calcium ions applied to the protein causes a conformational change to the protein that either directly releases light energy, as is in a calcium activated photoprotein finalizing the oxidation and release of its stabilized oxidized luciferin and light, or calcium ions binding to a luciferin binding or luciferin carrier protein, causes the luciferin carrier protein to release its stored luciferin in proximity or directly complexed with its luciferase or calcium activated photoprotein, and thus generate light by the oxidation of the luciferin within the luciferase or allowing renewal of spent (oxidized) luciferin by presentation to the photoprotein.

The present disclosure teaches new Coelenterazine analogs that significantly modify the color and activity of Coelenterazine utilizing luciferases, and calcium activated photoprotein light emission. The present invention discloses the use of novel techniques utilizing CAPS to enhance visual experiences of various audiences as listed above.

SUMMARY OF THE EMBODIMENTS

The disclosure teaches a composition, comprising a calcium reactive light emitting photoprotein dissolved or suspended in calcium-free and magnesium-free purified water, or other suitable buffer(s). The calcium reactive photoprotein(s) reacts with the calcium contained in or on a person's skin, clothes, hair, and/or any nearby or adjacent calcium containing environmental surfaces; wherein the contact of the photoprotein with the surface that contains calcium produces light visible to the dark adapted human eye during a theatrical, cinematic, or any type of staged production.

The disclosure further teaches the composition of claim 1, further comprising a combination containing a fluorescent protein, dye, or quantum dot, in order to produce color variations to the emitted light from the photoprotein as it reacts with calcium.

The disclosure further teaches a calcium activated photoprotein that has been manufactured using an analog of its naturally occurring luciferin chromophore which alters the color of the light emitted.

The disclosure further teaches delivering the composition by means of a storage reservoir connected with a water guiding apparatus, pump, or sprayer to deliver the photoprotein in a manually operated or automatic electronically controlled delivery system. The component(s) of the photoprotein system may include micro-encapsulation to alter the temporal emission of light by delaying the release of the photoprotein thereby delaying the photoprotein's contact with a calcium containing surface.

The composition is selected from natural or semi-synthetic photoproteins derived from Aequorin, Obelin, Halusterin, or Atollin, and/or any other calcium activated photoprotein that can be cloned and manufactured for use in entertainment applications. The calcium activated releasing protein can release its attached luciferin to supply additional substrate to regenerate or prolong the reaction generating emitted visible or ultraviolet invisible light. The calcium releasing protein can be manufactured containing an analog of its naturally occurring luciferin to alter the color, duration, or kinetics of the light emitted.

The disclosure further teaches Synthetic Coelenterazine analog methoxy-Coelenterazine.

The disclosure further teaches Synthetic Coelenterazine.

The disclosure further teaches Synthetic Coelenterazine analog methoxy-eCoelenterazine-Fluoride.

The disclosure further teaches Synthetic Coelenterazine analog eCoelenterazine-Fluoride.

The disclosure further teaches Synthetic Coelenterazine analog methoxy-vCoelenterazine-Fluoride.

The disclosure further teaches Synthetic Coelenterazine analog methoxy-vCoelenterazine.

The disclosure further teaches Coelenterazine analog vCoelenterazine-Fluoride.

The disclosure further teaches Synthetic Coelenterazine analog eCoelenterazine.

The disclosure further teaches the Synthetic analogs listed above used in conjunction with calcium activated photoprotein to alter the color of light generated.

The disclosure further teaches Synthetic analogs listed above used in conjunction with any coelenterazine type luciferase to alter the color of light generated.

The disclosure further teaches Synthetic analogs listed above used in conjunction with any calcium activated luciferin releasing protein to alter the color of light generated.

The disclosure further teaches Synthetic analog methoxy-eCoelenterazine-Fluoride used in conjunction with calcium activated photoprotein to alter the color of light generated.

The disclosure further teaches Synthetic analog methoxy-eCoelenterazine-Fluoride used in conjunction with any coelenterazine type luciferase to alter the color of light generated.

The disclosure further teaches Synthetic analog methoxy-eCoelenterazine-Fluoride used in conjunction with any calcium activated luciferin releasing protein to alter the color of light generated.

The disclosure further teaches Synthetic analog eCoelenterazine-Fluoride used in conjunction with any calcium activated photoprotein to alter the color of light generated.

The disclosure further teaches Synthetic analog eCoelenterazine-Fluoride used in conjunction with any Coelenterazine utilizing luciferase to spectrally alter the color of light generated by the reaction.

The disclosure further teaches Synthetic analog eCoelenterazine-Fluoride used in conjunction with any calcium activated luciferin releasing protein to spectrally alter the color of light generated by releasing the analog in proximity, within 10-100 nanometers for diffusion to a Coelenterazine utilizing luciferase.

The disclosure further teaches Synthetic analog vCoelenterazine-Fluoride used in conjunction with any calcium activated photoprotein to alter the color of light generated.

The disclosure further teaches Synthetic analog vCoelenterazine-Fluoride used in conjunction with any Coelenterazine utilizing luciferase to spectrally alter the color of light generated by their reaction.

The disclosure further teaches Synthetic analog vCoelenterazine-Fluoride used in conjunction with any calcium activated luciferin releasing protein to spectrally alter the color of light generated by releasing the analog in proximity to a Coelenterazine utilizing luciferase.

The disclosure further teaches Synthetic analog methoxy-eCoelenterazine-Fluoride used in conjunction with any calcium activated photoprotein in proximity with a fluorescent protein to alter the color of light generated as the proteins move into proximity with one another.

The disclosure further teaches Synthetic analog methoxy-eCoelenterazine-Fluoride used in conjunction with any coelenterazine type luciferase in proximity with a fluorescent protein to alter the color of light generated as the proteins move into proximity with one another.

The disclosure further teaches Synthetic analog methoxy-eCoelenterazine-Fluoride used in conjunction with any calcium activated luciferin releasing protein in proximity with a fluorescent protein to alter the color of light generated as the proteins move into proximity with one another.

The disclosure further teaches Synthetic analog eCoelenterazine-Fluoride used in conjunction with any calcium activated photoprotein in proximity with a fluorescent protein to alter the color of light generated as the proteins move into proximity with one another.

The disclosure further teaches Synthetic analog eCoelenterazine-Fluoride used in conjunction with any Coelenterazine utilizing luciferase in proximity with a fluorescent protein to alter the color of light generated as the proteins move into proximity with one another.

The disclosure further teaches Synthetic analog eCoelenterazine-Fluoride used in conjunction with any calcium activated luciferin releasing protein.

The disclosure further teaches Synthetic analog vCoelenterazine-Fluoride used in conjunction with any calcium activated photoprotein in proximity with a fluorescent protein to alter the color of light generated as the proteins move into proximity with one another.

The disclosure further teaches Synthetic analog vCoelenterazine-Fluoride used in conjunction with any Coelenterazine utilizing luciferase to spectrally alter the color of light generated by the reaction.

The disclosure further teaches Synthetic analog vCoelenterazine-Fluoride used in conjunction with any calcium activated luciferin releasing protein.

The compounds disclosed herein yield changes in the spectral properties of the Coelenterazine analog CTZ-v by Methoxy group modification. In addition to these spectral changes, compound V (Me-O-vCTZ-F) will also have a higher luminescent intensity with Ca2+ triggered luciferases like Aequorin.

The disclosure further teaches methods for use for novel synthetic analogs of Coelenterazine. Coelenterazine analogs can be used as a luciferin by some luciferases that also use coelenterazine as a substrate. Although coelenterazine is the natural substrate for *Gaussia* luciferase, it does not use the coelenterazine analogs. In circumstances where the independent use of two or more luciferases is desired, such as in the dual-luciferase reporter assays, the selective use of coelenterazine and coelenterazine analogs allows independent control of light production by different luciferases, one of which is Gaussia luciferase or a luciferase unable to use the coelenterazine analogs. One can envision the use of the analogs where the production of purple light is desirable. This includes applications where:

1) background fluorescence is attenuated or minimized by the use and production of purple light
2) the use of dyes or fluorescent proteins that are excitable by purple light and re-emit the light at a longer wavelength
3) for use where a light detector is more efficient at detecting wavelengths longer than purple and where this allow the detector to more efficiently detect shifted, longer wavelength light such as in FRET or BRET applications
4) the detection of binding events in in vitro diagnostics applications
5) in environmental and chemical sensors
6) in reporter assays
7) cell surface labeling for in vitro or in vivo visualization of cells
8) for detection of molecules in solutions or within cells
9) where the purple wavelength is able to excite membrane associated proteins to create a pore or other conformational change such as optogenetics applications of channel rhodospsin
10) where the purple wavelength is able to create a covalent binding event between two molecules such as a protein with another protein, a protein with a dye or reactive label, or any combination of organic and inorganic molecules that are able to be activated for reactions using purple light
11) where purple light generates free radicals that can be used to generate light for detection of molecular proximities or binding events; and/or, 12) where purple light generates free radicals that can be used to inactivate or destroy pathogenic cells such as cancer or pathogenic bacteria.

The disclosure further teaches a composition of a Calcium Activated Photoprotein applied to the eye containing soft contact lenses previously impregnated with calcium salts to make the contact lenses emit light. The disclosure further teaches a method of treating a contact lens a composition of a Calcium Activated Photoprotein applied to the eye containing soft contact lenses previously impregnated with calcium salts to make the contact lenses emit light.

The disclosure further teaches a composition of a Coelenterazine utilizing luciferase and Calcium activated Coelenterazine releasing protein applied to the eye containing soft contact lenses previously impregnated with calcium salts to make the contact lenses emit light. The disclosure further teaches a method of treating a contact lens with a composition of a Coelenterazine utilizing luciferase and Calcium activated Coelenterazine releasing protein applied to the eye containing soft contact lenses previously impregnated with calcium salts to make the contact lenses emit light.

The disclosure further teaches a composition of a Coelenterazine utilizing luciferase and Calcium activated Coelenterazine releasing protein photoprotein for medical visualization of the cornea for diagnostic evaluation and visualization. The disclosure also teaches a method of use of treating a contact lens with a composition of a Coelenterazine utilizing luciferase and Calcium activated Coelenterazine releasing protein photoprotein for medical visualization of the cornea for diagnostic evaluation and visualization. The disclosure further teaches a kit comprising a contact lens with a composition of a Coelenterazine utilizing luciferase and Calcium activated Coelenterazine releasing protein photoprotein for medical visualization of the cornea for diagnostic evaluation and visualization.

The disclosure further teaches a Coelenterazine pill, wherein the Coelenterazine pill is Coelenterazine or a Coelenterazine analog. The disclosure further teaches a coelenterazine pill that is water soluble. Water solubilization is taught in Bioluminescence: chemical principles and methods/Osamu Shimomura, 2006 by World Scientific Publishing Co. Pte. Ltd., page 167, herein incorporated by reference in its entirety.

The disclosure further teaches a luciferase pill. The disclosure further teaches a luciferase pill that is water soluble.

The disclosure further teaches use of water-soluble Coelenterazine and its analogues as described above to include, but are not limited to: life science research including in vitro and in vivo imaging of luciferases, diagnostic devices, novelty applications like bath tub products, foam-party products, fish-food tablets, squirt guns.

The disclosure further teaches the dispensation of water-soluble Coelenterazine and its analogues as described above in a two chambered water gun, as disclosed herein, and as described in U.S. Pat. No. 6,247,995. The disclosure further teaches adding a coelenterazine pill to the water gun, and a luciferase pill to the water gun, wherein in the activation of the water gun, the Coelenterazine and luciferase are mixed.

The disclosure further teaches a composition comprising Coelenterazine or its analogues in a water-soluble form, compressed into a quick dissolving pill/capsule format containing: a) excipients not limited to but including: Mannitol, Trehalose, Sucrose, Lactose, Glucose, Xyliol, Erythritol, Maltose, Maltitol, Sorbitol, Pullulan, Hydroxycellulose, Methylcellulose, Propylcellulose, & Poloxamer, Cycloamyloses polymers like b-Hydroxycyclodextrin, cyclodextrin, hydroxypropyl-beta cyclodextrin, alpha-cyclodextrins, other cycloamyloses, Poloxamers, Polythyleneglycol, Polyvinylpyrolidinone, and Polyvinyl alcohols, b) rapid disintegrants may include, but are not limited to, Crospovidone, Povidone, Microcrystalline Cellulose, Croscarmellose, Carboxymethylated Potato Starch, Tapioca, Inulin, Chicory Root Starch, Corn Starch, Sodium Starch Glycolate, Malic Acid, Oxalic Acid, Citric Acid, Sodium Bicarbonate, amino acid disintegrates such as L-alanine HCL, L-lysine, glycine, L-arginine, L-tyrosine. c) enzymatic activity modulators that include but are not limited to Potassium Bromide, Magnesium Bromide, Potassium Iodide, Sodium Chloride, Potassium Chloride, Sodium Iodide, and physiologic buffering agents, such as Tris Base and Tris, Sodium Phosphate, Sodium Phosphate, and d) binding agents that include but not limited to: Stearic Acid, plant saturated fatty acids, such as Cocoa Butter, Mango Butter, Shea Butter, Argan Oil, Ucuuba Butter, Acai Butter, Kokum Butter, Tucuma Butter, Capralyl Glycol, Murumuru Butter, or Illilpe Butter and/or e) Coelenterazine stabilizer, that include but are not limited to: TECP, Sodium Thiosulfate Pentahydrate, Ascorbic Acid, DTT, Tocopherol. The disclosure further teaches said composition wherein the Coelenterazine is combined with luciferases derived from *Gaussia princeps* or *Renilla reniformis* mixed with a buffer system in a pill or capsule format. The disclosure further teaches said composition, wherein the tablet format is used in a two-chambered squirt gun as described in U.S. Pat. No. 6,247,995, incorporated by reference herein in its entirety, combined with a *Gaussia* and/or *Renilla* luciferase systems.

DETAILED DESCRIPTION

Figure 1:
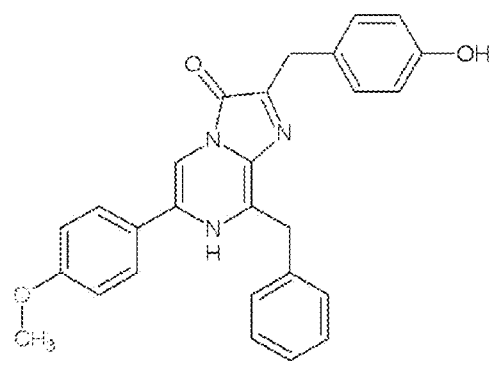
FIG. 1 is chemical structure of Methoxy-Coelenterazine (Me-O-CTZ).
Figure 2:
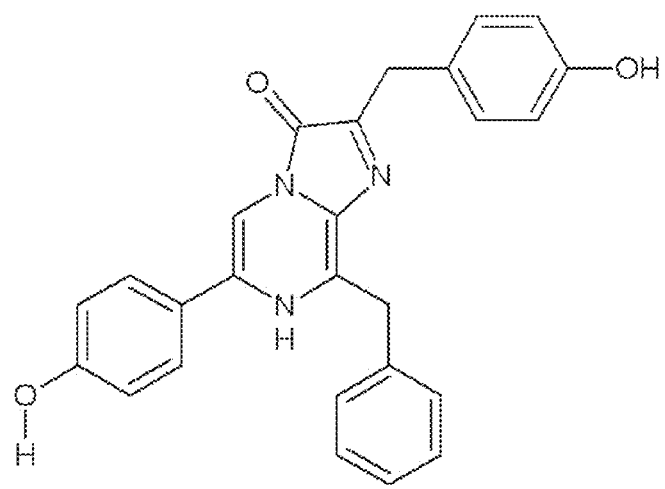
FIG. 2 is chemical structure of Coelenterazine (CTZ).
Figure 3:
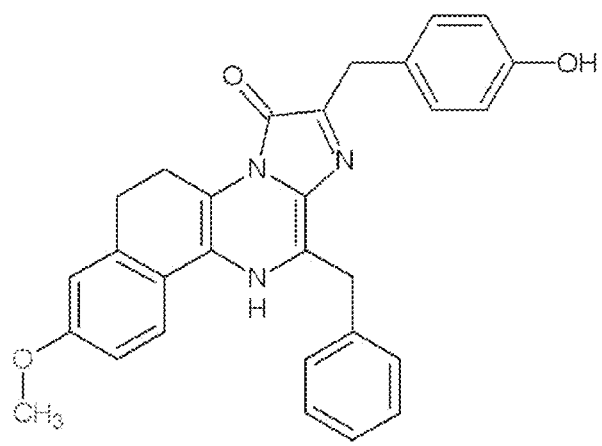
FIG. 3 is chemical structure Methoxy-e-Coelenterazine (Me-O-eCTZ).
Figure 4:
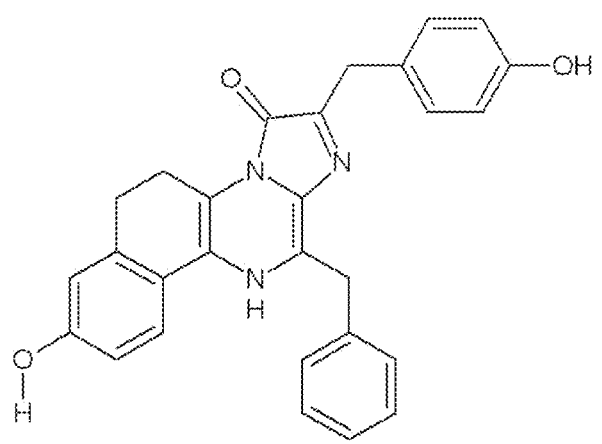
FIG. 4 is chemical structure e-Coelenterazine (eCTZ).
Figure 5:
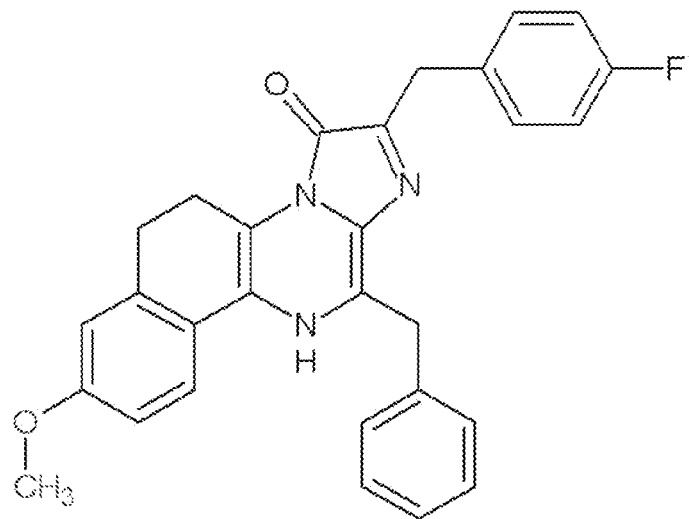
FIG. 5 is chemical structure Methoxy-eCoelenterazine-Fluoride (Me-O-eCTZ-F).
Figure 6:
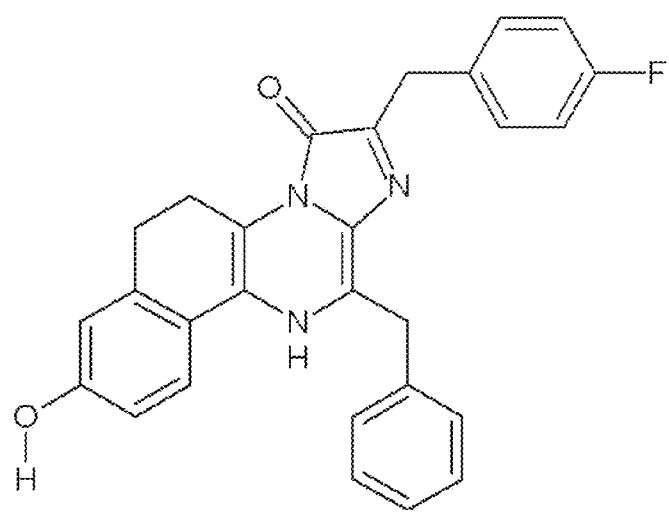
FIG. 6 is chemical structure e-Coelenterazine-Fluoride (eCTZ-F).
Figure 7:
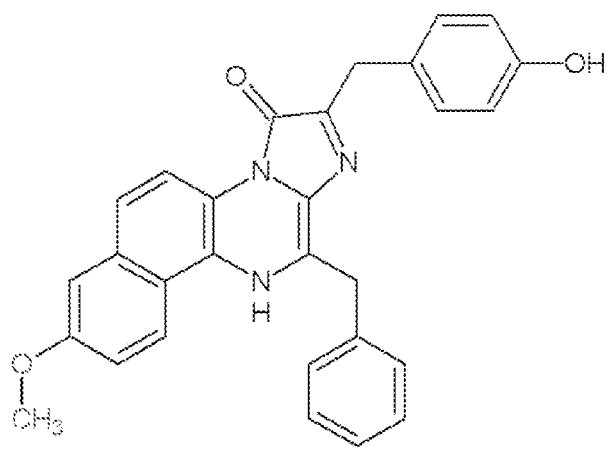
FIG. 7 is chemical structure Methoxy-v-Coelenterazine (Me-O-vCTZ).
Figure 8:
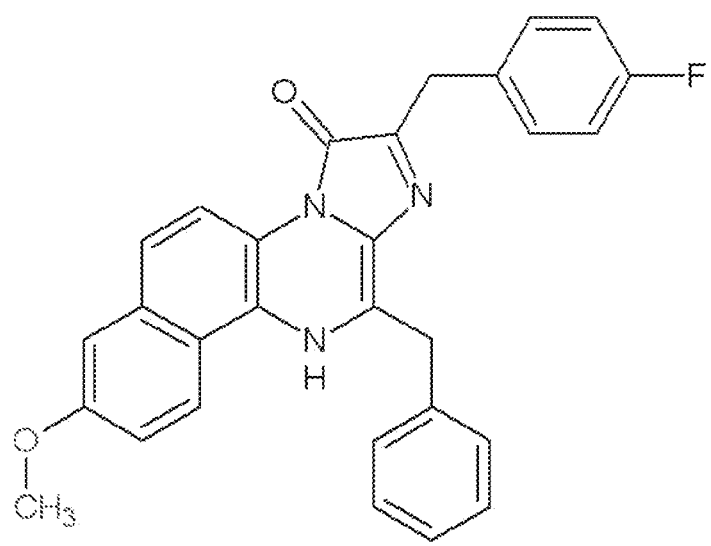
FIG. 8 is chemical structure Methoxy-v-Coelenterazine-Fluoride.

Unless otherwise indicated, all numbers expressing quantities of ingredients, dimensions reaction conditions and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

CAP is a phenomenon in which light energy is specifically channeled from a semi-oxidized or partially oxidized metastable high energy luciferin molecule contained within its folded conformation upon contact with calcium ions.

Calcium releasing proteins (herein known as CARP) are proteins that store a luciferin or synthetic luciferin analog, and upon contact with calcium ions release their stored or bound luciferin.

Many calcium activated photoproteins have been discovered since the discovery by Dr Osamu and Akemi Shimomura of the protein known as Aequorin from their early work in 1968 collecting green glowing jellyfish classified as *Aequoria victoria* or *Aequoria funkalsrud* from the docks of Friday Harbor Marine Biological Laboratory in Washington, USA.

Many other CAPs have been discovered since 1968, the most prominent ones and the ones best characterized chemically and cloned are Obelin from *Obelia geniculata*, Mitrocomin, Mnemiopsin, Halisturin (from a sea cucumber *Halisturia*), Berovin from *Beroe ovata*, Atollin (from *Atolla wyvillei*) are all similar in their response to a local increase in calcium ions; they release bright blue visible light when in contact with calcium ions.

CAPs are manufactured using molecular biology to engineer recombinant bacteria to produce large amounts of these proteins by those skilled in the art. The CAPS listed above and many other calcium activated photoproteins can be used in entertainment and research applications. The best known, most studied, and most stable CAPS is Aequorin.

Suitable buffers include, but are not limited to: calcium-free and magnesium-free purified water, distilled water of neutral pH, 0.0001-0.1 molar EGTA solutions, 0.0001-0.1 molar EDTA solutions, as long as the pH is within the range of CAPs activity.

Reactive calcium may be contained in or on a person's skin, clothes, hair, and/or any nearby or adjacent calcium containing environmental surfaces. The calcium concentration should reach a local threshold that will trigger the CAPs to emit light, which is in the local environment and in a range of 0.00001-0.1 molar calcium once in contact with the CAPs.

Light visible to the dark adapted human eye includes the visible spectrum, from 400-750 nanometer wavelengths.

Synthetic Coelenterazine analogs include, but are not limited to methoxy-eCoelenterazine-Fluoride, eCoelenterazine-Fluoride, methoxy-vCoelenterazine-Fluoride, vCoelenterazine-Fluoride, Fluoro-eCoelenterazine-Fluoride, and Fluoro-vcoelenterazine-Fluoride.

The most prevalent substrate luciferin molecule found in nature is a high energy dioxetanone molecule called Coelenterazine, named after the coelenterate animals they were found to be associated with. The light emitting reaction proceeds as Coelenterazine (or analog thereof) is combined with molecular oxygen to form an oxidation product, called Coelenteramide, and releases one carbon dioxide molecule and generates blue light at 480-490 nm (or a different color of light depending on analog used).

Figure 9:
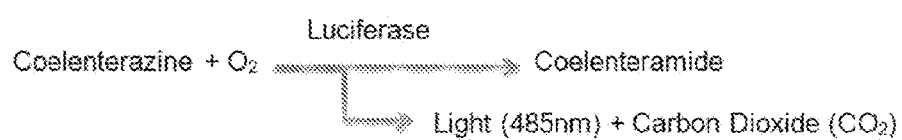
FIG. 9 is scheme of chemical reaction producing Coelenteramide, Light & $CO_2$.
Figure 10:
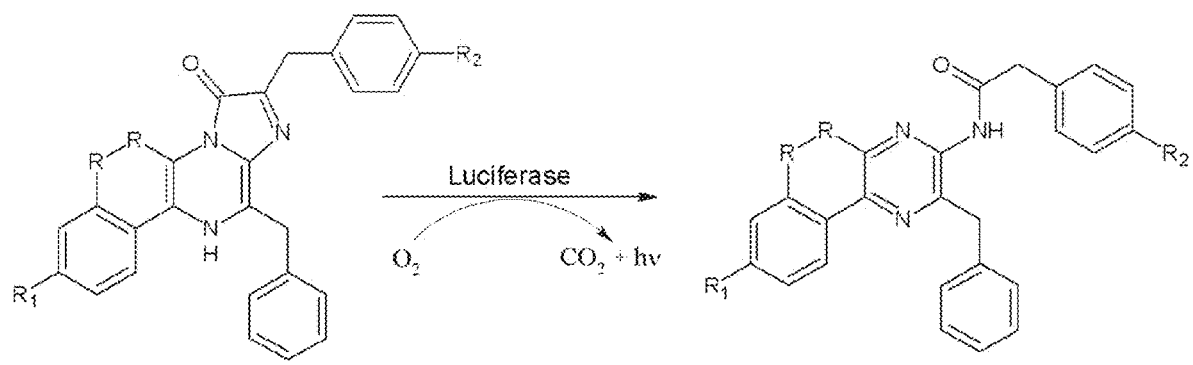
FIG. 10 is chemical structure of reaction producing Coelenteramide, Light, & $CO_2$.
Figure 11:
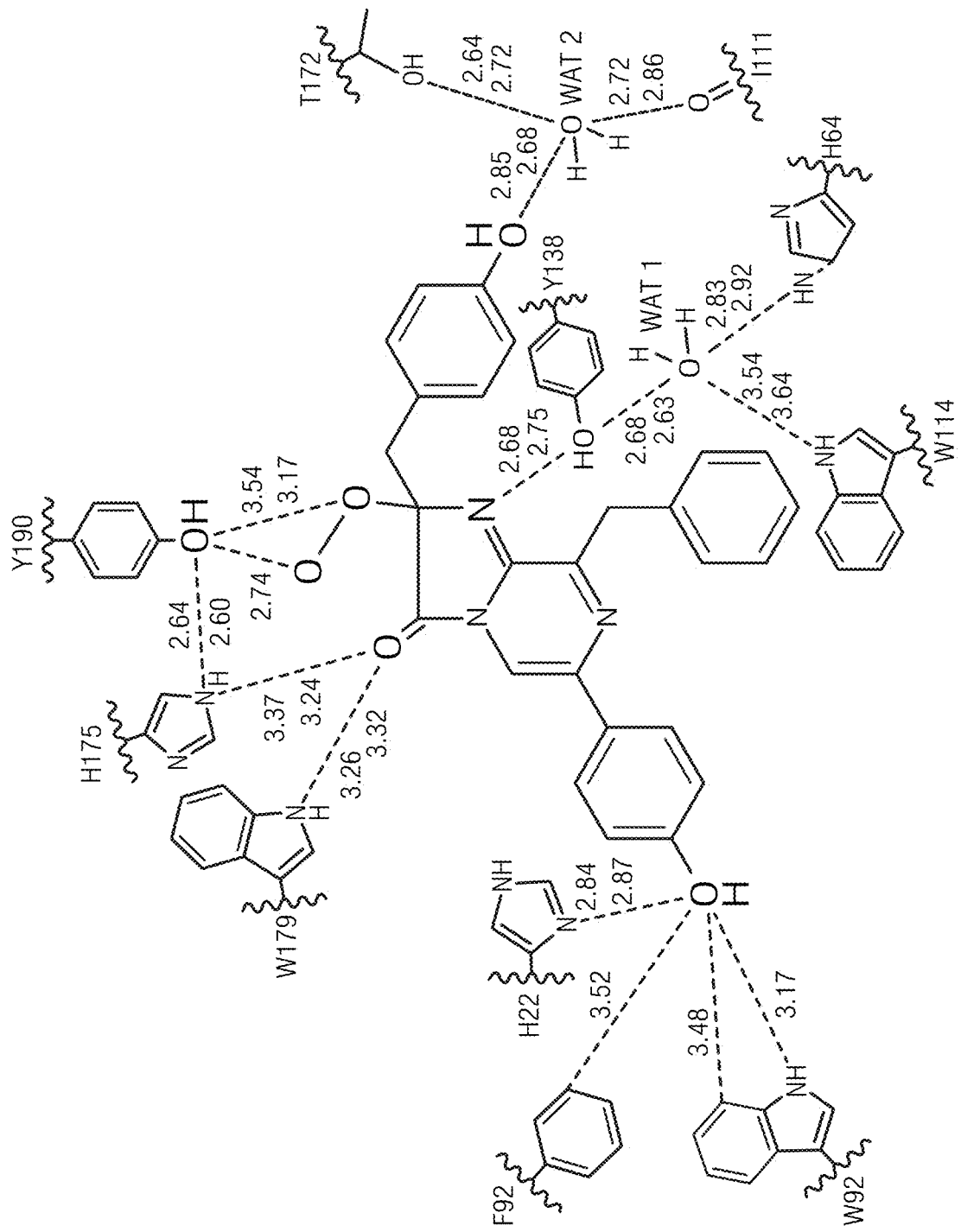
FIG. 11 is chemical structure of metastable hydroperoxy luciferin state within calcium active site.
Figure 12:
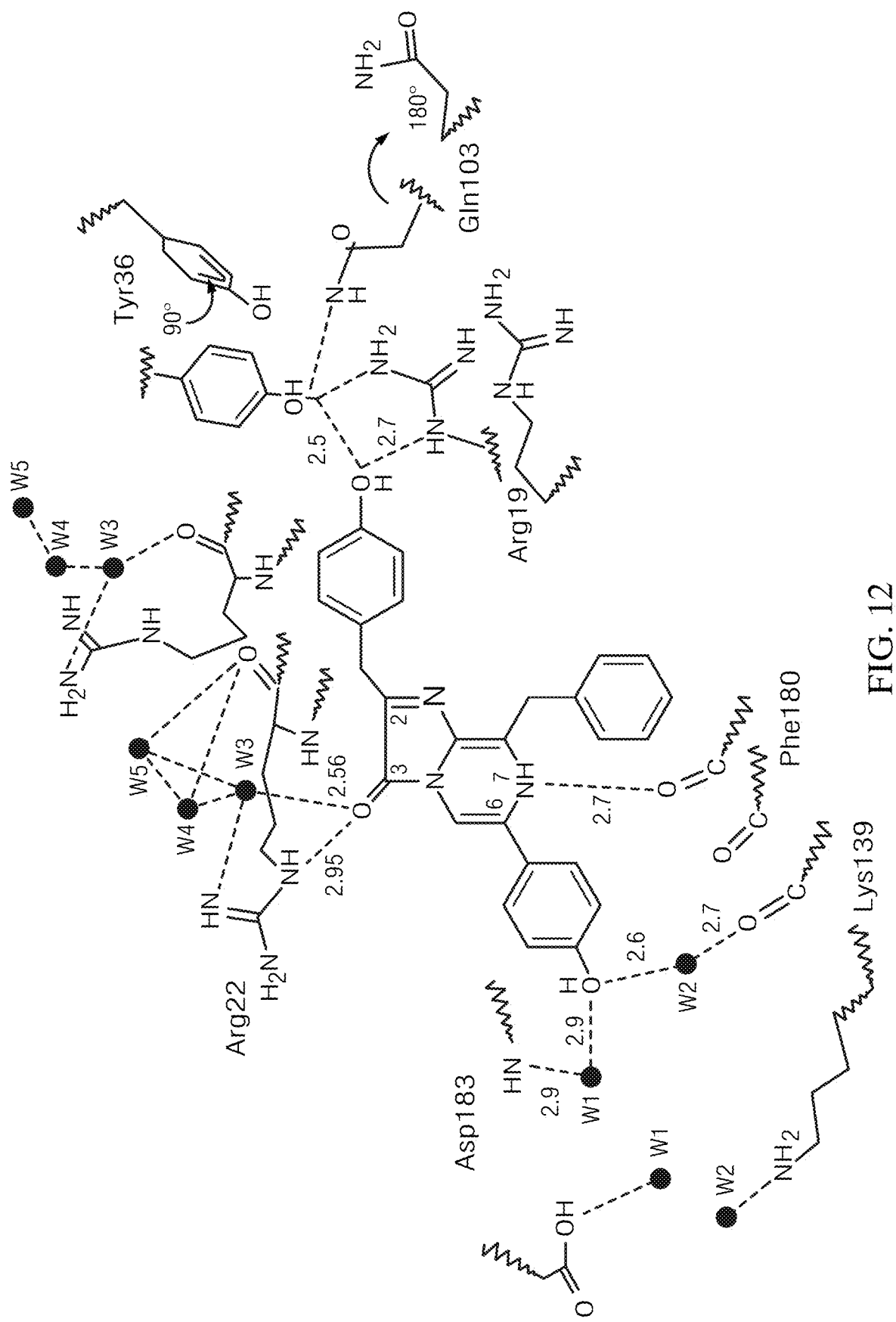
FIG. 12 is Coelenterazine held in "pocket" of Calcium Activated Coelenterazine Releasing Protein (CARP).

The general reaction for all Coelenterazine luciferins and their corresponding Coelenterazine utilizing luciferases is shown in FIG. 9.

Calcium activated photoproteins (CAPs) differ from Coelenterazine utilizing luciferases in that the luciferase constantly turns over the reaction to produce a steady light with the kinetics of standard enzymatic mechanisms. Michaelis-Menton kinetics apply to these enzymatic reactions; as products of the reaction are produced they may lower the turnover by competitive inhibition with a steady drop in light production.

The light production mechanism is different with CAPs. CAPs usually release light only once upon binding with calcium ions, unless more substrate is present in their environment, then CAPs can become "pseudo-luciferases" and turnover slowly emitting light under first order Michaelis-Menton kinetics.

Within the active site of a calcium activated photoprotein the substrate Coelenterazine (or analog luciferin) is held in a metastable hydroperoxy luciferin state, and calcium ion triggers the completion of the oxidation to the amide and the release of light.

When the partially oxidized Coelenterazine (or analog) is held in this state as it slowly forms during the manufacturing process, it becomes stable. The molecule can be freeze or spray dried under appropriate reduced pressure conditions known to those skilled in the art, to obtain a very long lasting, active, dry yellowish-white powder that is quite stable for many years if kept cool and dry or frozen.

To activate the dried CAP, the CAP is dissolved in distilled water, or calcium and magnesium free water that is substantially free of inhibitors. More preferably, the water is at a pH between pH 7 and pH 8 for a highly active light emitting solution. The reaction is retarded and the light output is prolonged using competition with magnesium salts, usually Magnesium Chloride ($MgCl_2$) added to the solution to compete for the calcium binding sites on the CAP and delay the light emission over time; however, this will also diminish the brightness.

Retarding the reaction is achieved by lowering the environmental concentration of calcium ions that would come into contact with the CAP. Divalent metal ion chelators can be used such as ethylenediamine-tetracetate (EDTA), Ethyleneglycoltetracetic acid, (EGTA), and phosphates that would irreversibly bind calcium. Any molecules that lower the concentration and/or availability of calcium ions preventing their interaction with the calcium binding domains of the CAP will work.

The present disclosure teaches that the color of the reaction is altered by using an analog of Coelenterazine, used in the manufacture of the CAP which imparts desirable changes to the brightness and temporal kinetics of the light produced. Certain CAPs manufactured with different analogs may retard the reactivity of the CAP to environmental calcium, as in the case of Coelenterazine-Iodide which prolongs light emission, by delayed "spring-opening" of the CAPs to prolong the light output for longer duration of time, over tens of minutes. As can be seen from the chart below, not only can color be altered, but also the time for half of all the available light energy to be released can be altered, changing the brightness of the light perceived by the human observer. A partial listing is included here in Table 1.

TABLE I

| Coelenterazine Analog | Em (nm) | RLC* | Relative Intensity † | Half-Rise Time ‡ (ms) |
|---|---|---|---|---|
| native | 466 | 1.00 | 1 | 6-30 |
| cp | 442 | 0.63 | 28 | 2-5 |
| f | 472 | 0.80 | 20 | 6-30 |
| h | 466 | 0.75 | 16 | 6-30 |
| hcp | 445 | 0.65 | 500 | 2-5 |
| n | 468 | 0.25 | 0.15 | 6-30 |

As seen from Table 1, blue or red color shifts are made by substituting synthetic Coelenterazine analogs for the naturally occurring Coelenterazine. These may also be used favorably to that change the response times upon contact with calcium ions which can substantially change relative intensity and brightness or the quality of the light generated upon contact with a calcium containing surface.

In nature, marine animals change the color of the light they produce by complexing the light producing protein, e.g. luciferase, or CAP, with a Fluorescent Protein designed to accept the light energy from the oxidation of Coelenterazine and transfer that excited state to an acceptor Fluorescent Protein that emits the light energy of the color desired by the animal.

In coastal waters where there indwelling light passes through a lot of green algae, the light reaching the bottom is much greener in color than areas of open-ocean where the light is predominantly blue. Marine animals have evolved to produce light of a color that maximally penetrates the water if they are using the light to attract other predators to themselves when they themselves are being grazed upon hoping to attract a larger predator at some distance to investigate and rid them of the grazer. In order to do this, and for other reasons still unknown, many sea pens, soft corals, and jellyfish, make specialized bioluminescent systems incorporating several proteins combined to make light of a certain color under nervous control.

Fluorescent Proteins have been well studied; are barrel proteins that contain a hydrophobic region that excludes water wherein the fluorescent chromophore resides. These molecules are designed to fit neatly in a complex with a CAP and produce light by the release of light energy from the CAP, without transmission of a blue photon intermediate, into the Fluorescent Protein directly; which evolved to obtain the color desired for the local conditions of the animal's residence.

In the Sea Pansy, *Renilla* species, the animal has a specialized photogenic area that contains a complex of Luciferase, Green Fluorescent Proteins, and recently cloned and fully described Calcium Activated Coelenterazine Releasing Protein. Calcium binding causes release of the substrate Coelenterazine, its luciferin, in proximity to its luciferase, causing the light emitting reaction to occur by the release of calcium under changes in membrane permeability or by direct nervous controlled release of calcium ions by the animal.

Calcium Activated Releasing Protein

As originally described by Charbonneau and Cormier in 1979, they discovered that the luciferin, Coelenterazine, isolated from the *Renilla* (Sea Pansy) was associated with an 18,500 MW protein recently cloned and crystallography reveals a dimeric protein of 186 amino acids containing four calcium binding EF-hand elements. Each subunit releases a Coelenterazine molecule upon binding with two (2) calcium ions. Coelenterazine is held in a protected and stabilized state to prevent it from being oxidized by the environmental oxygen.

Coelenterazine held in the "pocket" of the Calcium Activated Coelenterazine Releasing Protein (CARP) in the historical literature called this protein by different names; for the embodiments mentioned herein, we refer to any protein that stores Coelenterazine (or analog) and releases it into the environment upon contact with a Calcium Activated Coelenterazine Releasing Protein (CARP). For entertainment purposes this protein will only be used as a carrier of the Coelenterazine (or analog) in order to use the fact that the light emission can be turned on only under the control of environmental calcium and is not being used as a straight mixed luciferase-luciferin reaction as described in literature.

CARPs can be used to both control and extend the lifetime of the light emitting reaction between CAP and environmental calcium ion by creating a "pseudo-luciferase" out of the CAP. Once calcium enters the CAP binding sites the CAP starts to oxidize the luciferin and generate light.

Coelenterazine (or analog) can be added to the CARP at the same time the CAP is made by making a mixture of the two proteins in calcium free solutions and adding Coelenterazine (or analog) to the mixture and allowing the hydroperoxy-Coelenterazine CAP to form.

In the same calcium free solution and at the same time the CARP binds and holds the Coelenterazine (or analog) and CARP folds around the Coelenterazine. The completed reaction is determined by careful addition of Coelenterazine (or analog) and hourly luminomter testing. As the CARP or CAP incorporates Coelenterazine, the free Coelenterazine in solution goes down. The amount of Coelenterazine combined with CAPs and CARPs can be determined, with a 1 milligram/milliliter solution of *Renilla* or *Gaussia* Luciferase to monitor the absorption of Coelenterazine (or analog) as the CARP and CAP remove them from solution during folding and formation, the amount of light generated on mixing the solution in a luminometer will go down, indicating that the free Coelenterazine has been taken up by the CARP or CAP formation.

Different colors can be made at the same time by the addition of Fluorescent Proteins to the mixture and drying. During manufacturing in calcium free solutions, the CAP and the CARP are mixed together at the same time and then the mixture is freeze or spray dried. The resultant composition can be encapsulated as part of, or after the drying process, and different types of delays in light release are made by altering the thickness of the encapsulating film if chosen.

EXAMPLES

The following examples are provided for illustrative purposes only and are not intended to limit the scope of the invention.

Example 1

Using Coelenterazine Analogs for Unusual Color Effect

The qualities of the CAP as it is contemplated for use in any entertainment application would be empirically determined by experimentation. A scene from a space setting would require a shower of stars in deep blue; the natural analog of Coelenterazine would be used.

The next scene of the movie require a red rocket effect or firework effect a red fluorescent protein manufactured with the CAP substituted with vCoelenterazine-Fluoride would be used to splash onto the audience to make it appear to the people being entertained that they have been "fired" upon.

The duration of the theatrical effect can be prolonged by adding magnesium ions or adding small amounts of EDTA or EGTA solutions such as from 0.0001-0.005 molar EDTA to the CAPs or CARPs solution to delay the binding of calcium ions that activate the light emitting reaction.

Example 2

Mutations Made to CAPs to Alter Color Effect

To further alter the color of emitted light from the CAP is to use a mutated CAP in which amino acid substitutions have been made to modify the sequence of amino acids in the CAP protein itself.

Figure 13:
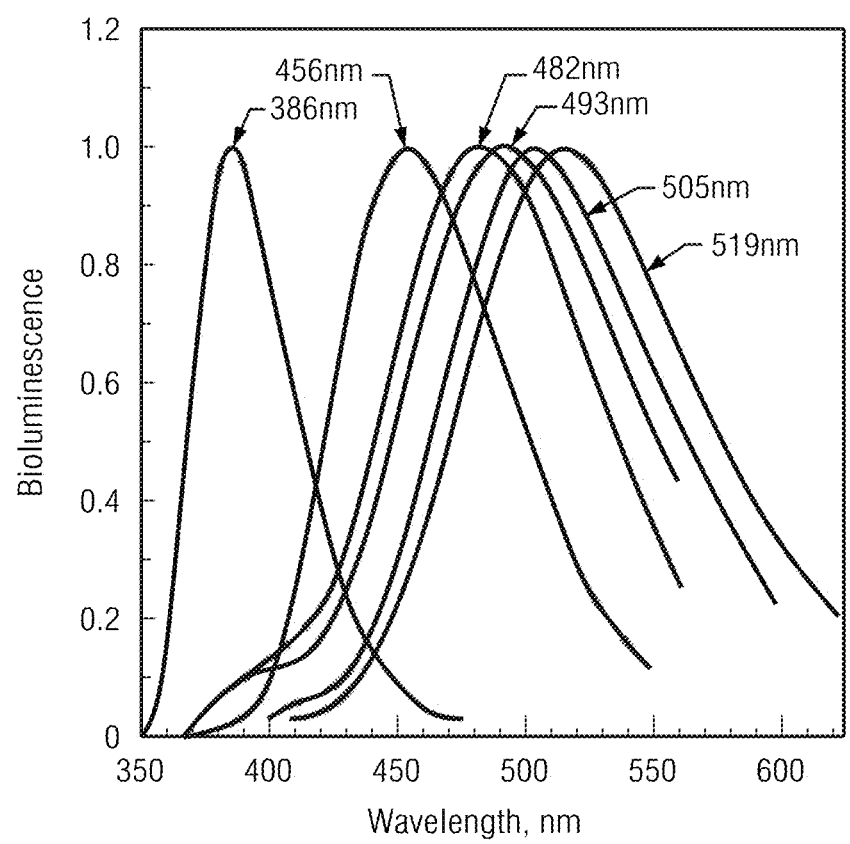
FIG. 13 is Obelin bioluminescence "rainbow" resulting from mutations of binding site residues with labeled spectral maxima.
Figure 14:
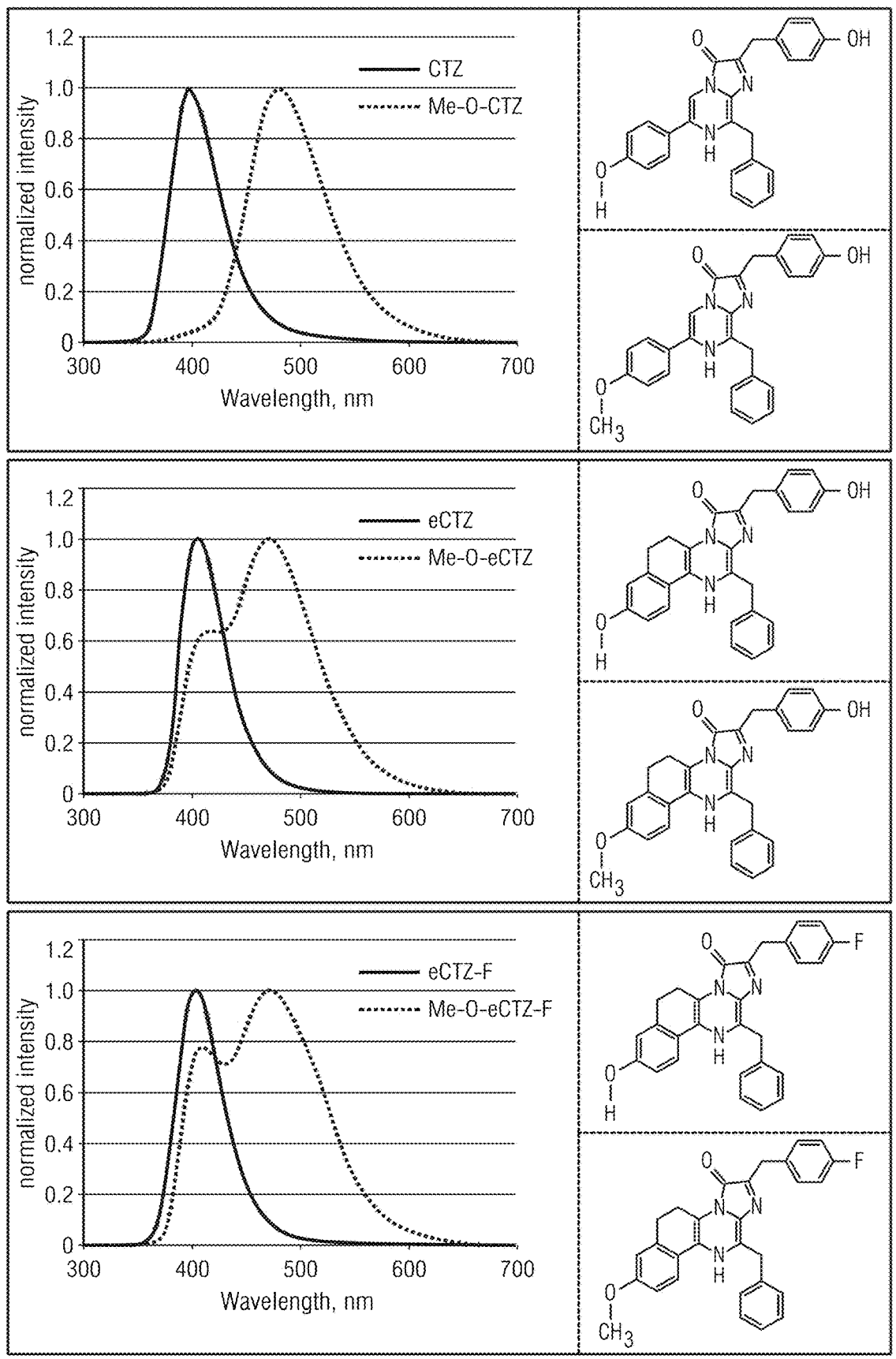
FIG. 14 is Emission Spectrum of *Renilla muelleri* Luciferase with different Coelenterazine analogues.
Figure 15:
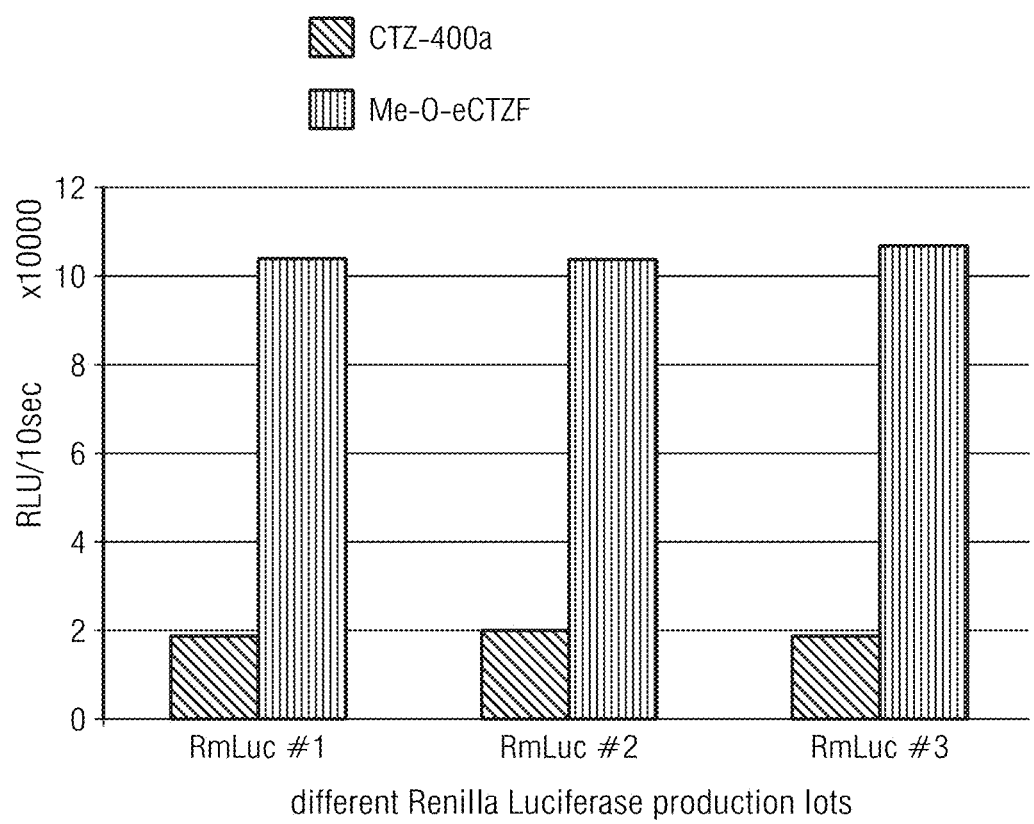
FIG. 15 is activity of *Renilla muelleri* Luciferase with Me-O-eCTZF in comparison to Coelenterazine 400a (aka Deep Blue C).
Figure 16:
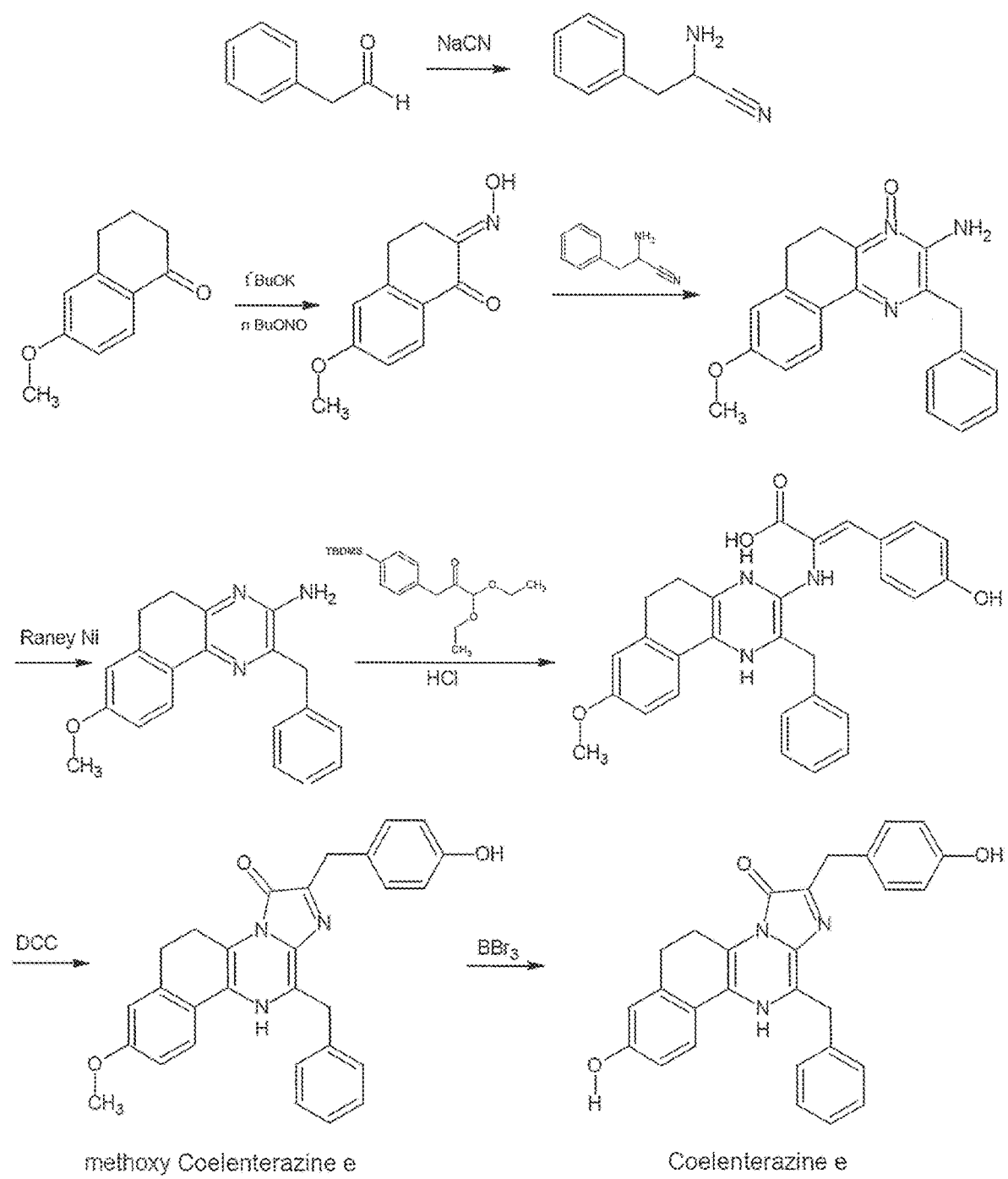
FIG. 16 is Coelenterazine E Synthesis.
Figure 17:
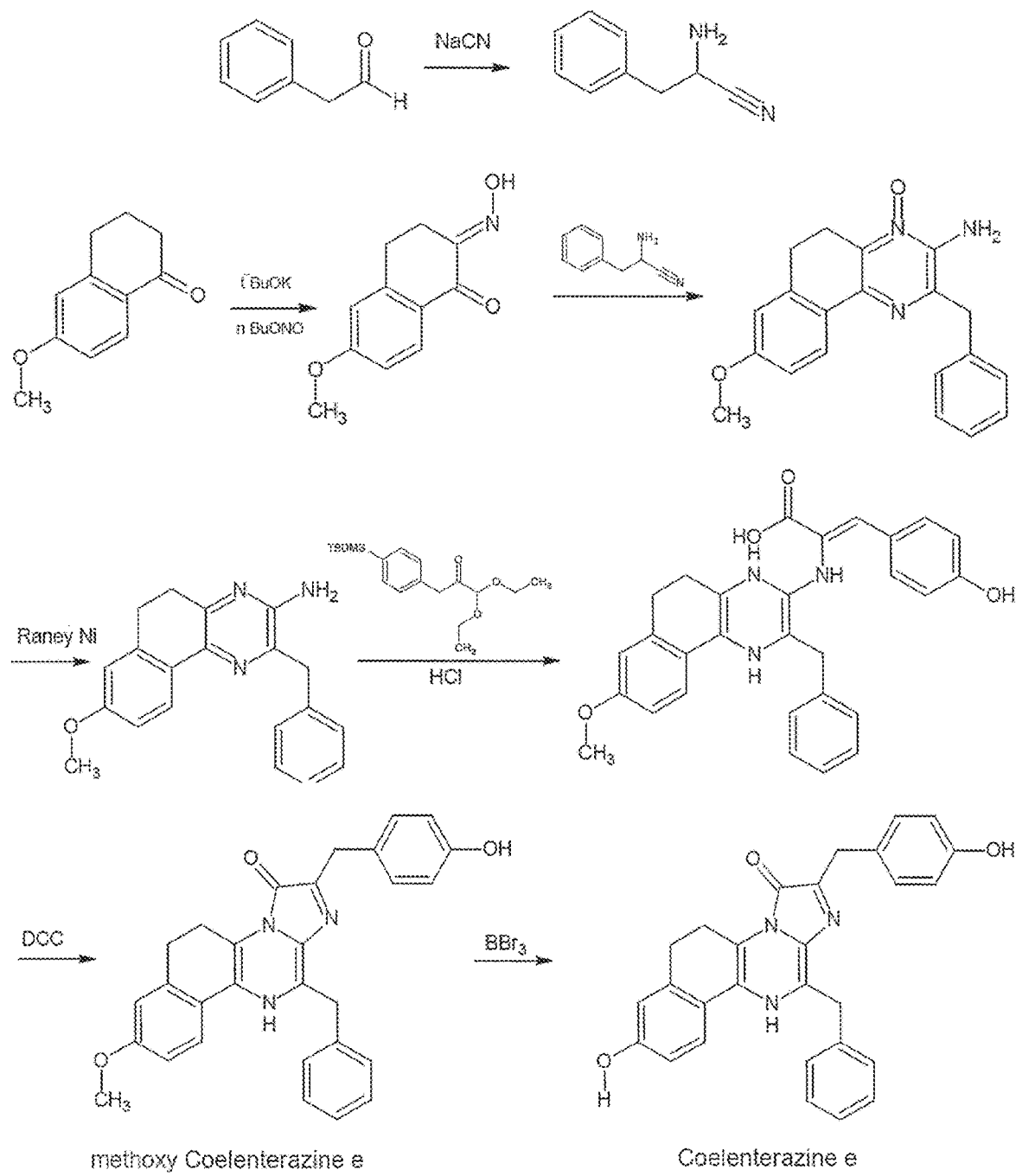
FIG. 17 is eCoelenterazine F Synthesis.
Figure 18:
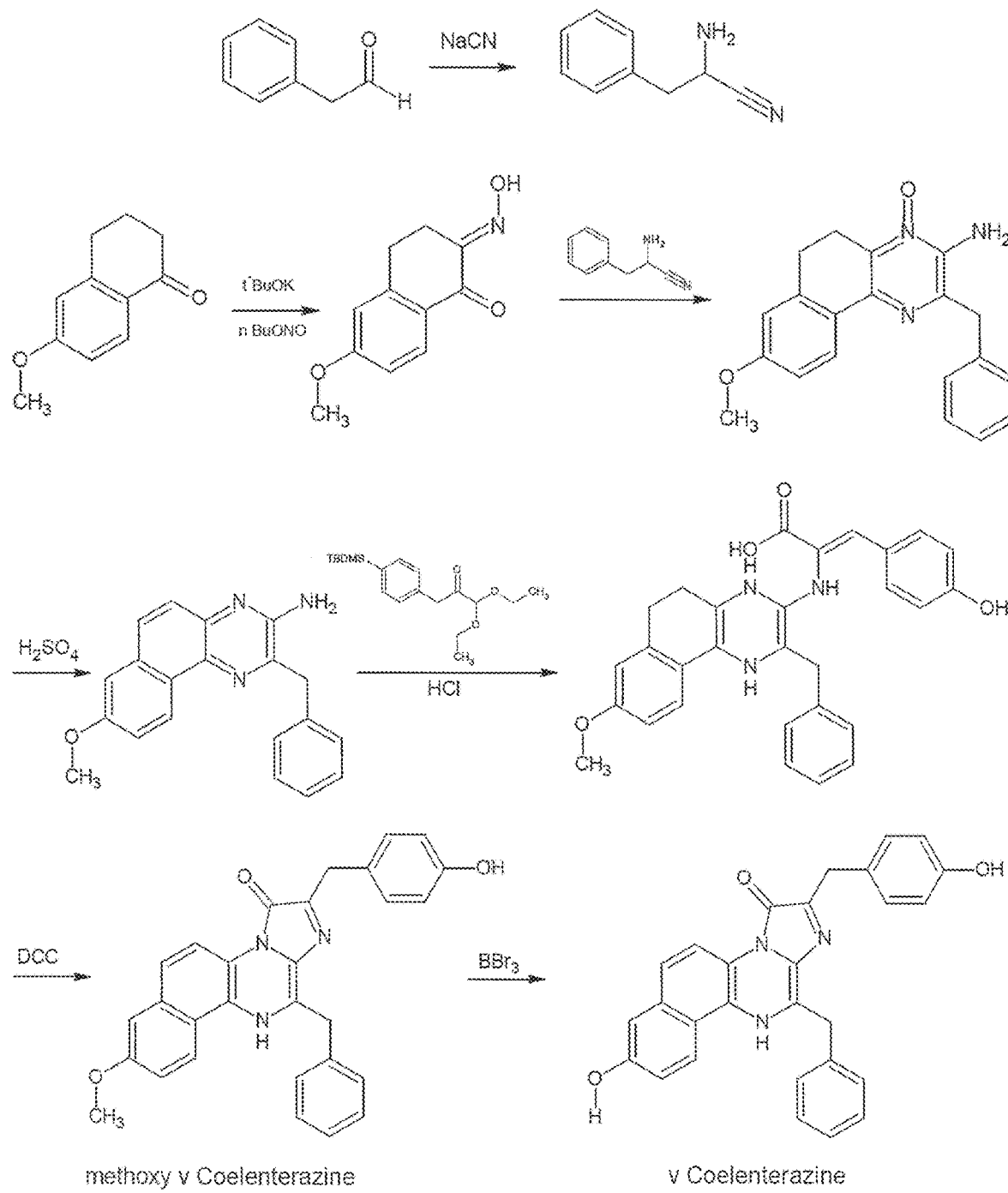
FIG. 18 is vCoelenterazine Synthesis.
Figure 19:
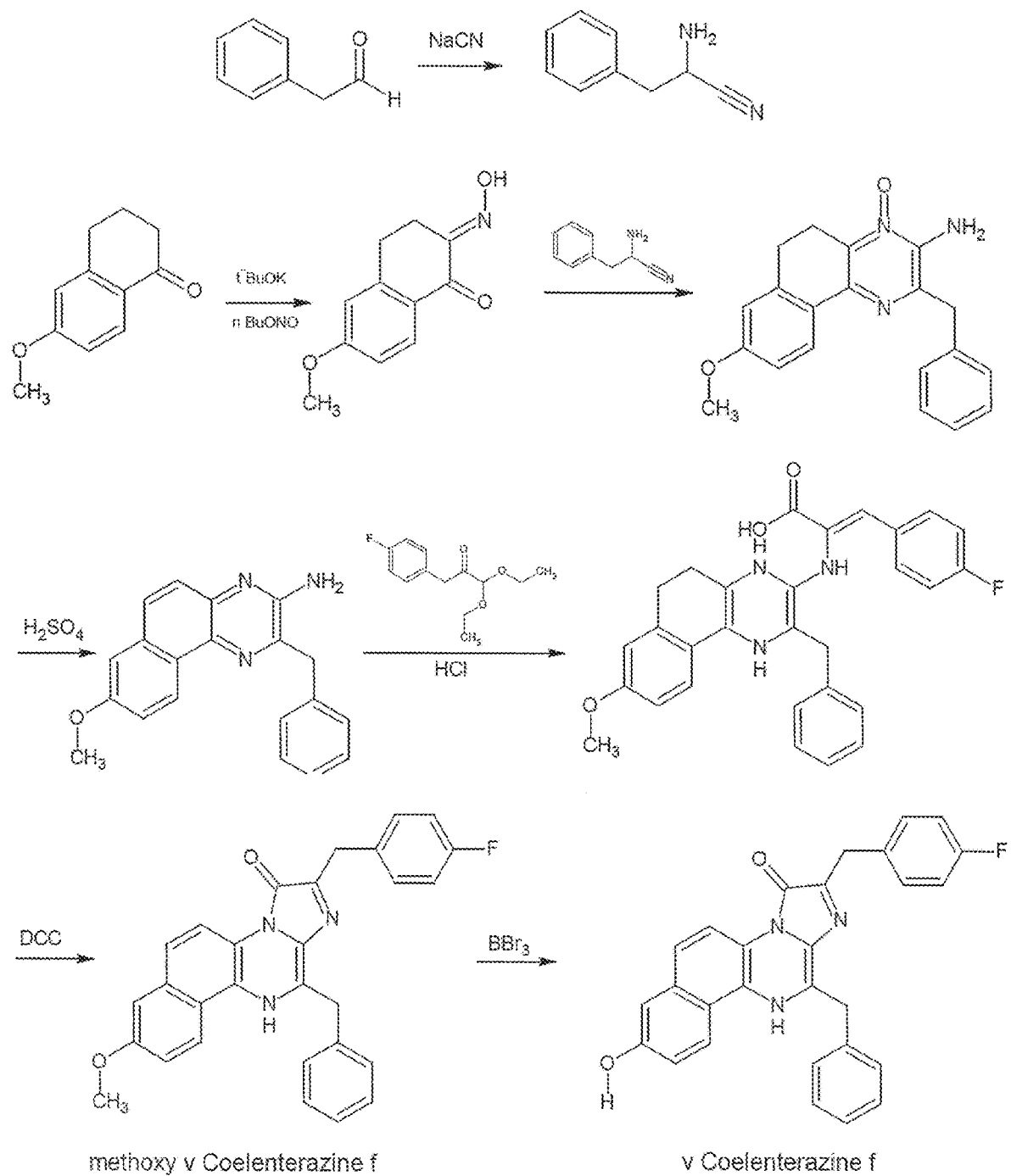
FIG. 19 is v Coelenterazine F synthesis.
Figure 20:
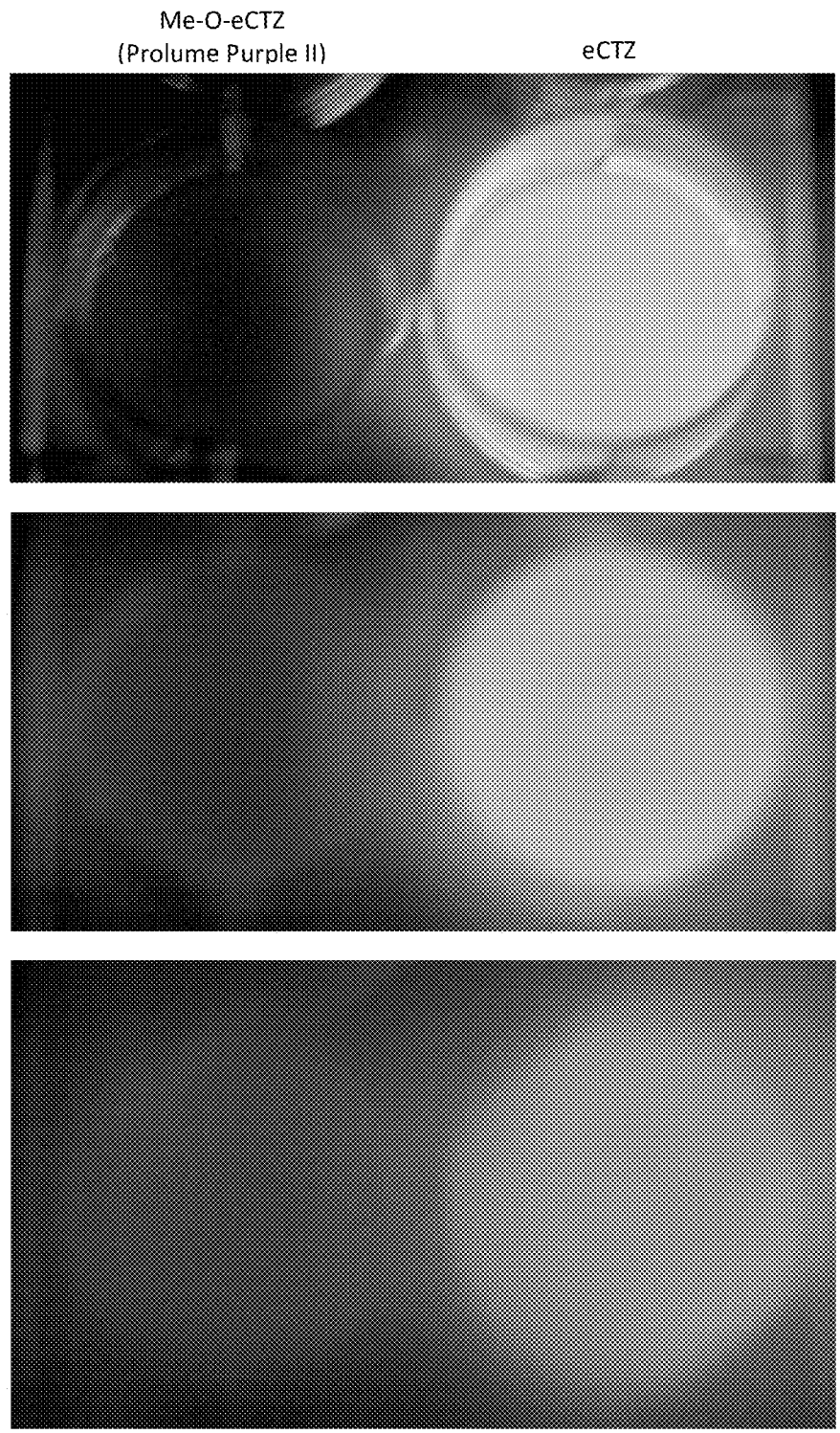
FIG. 20 is the light spectrum photo of Me-O-eCTZ. *Renilla mulleri* luciferase was used as a luciferase.
Figure 21:
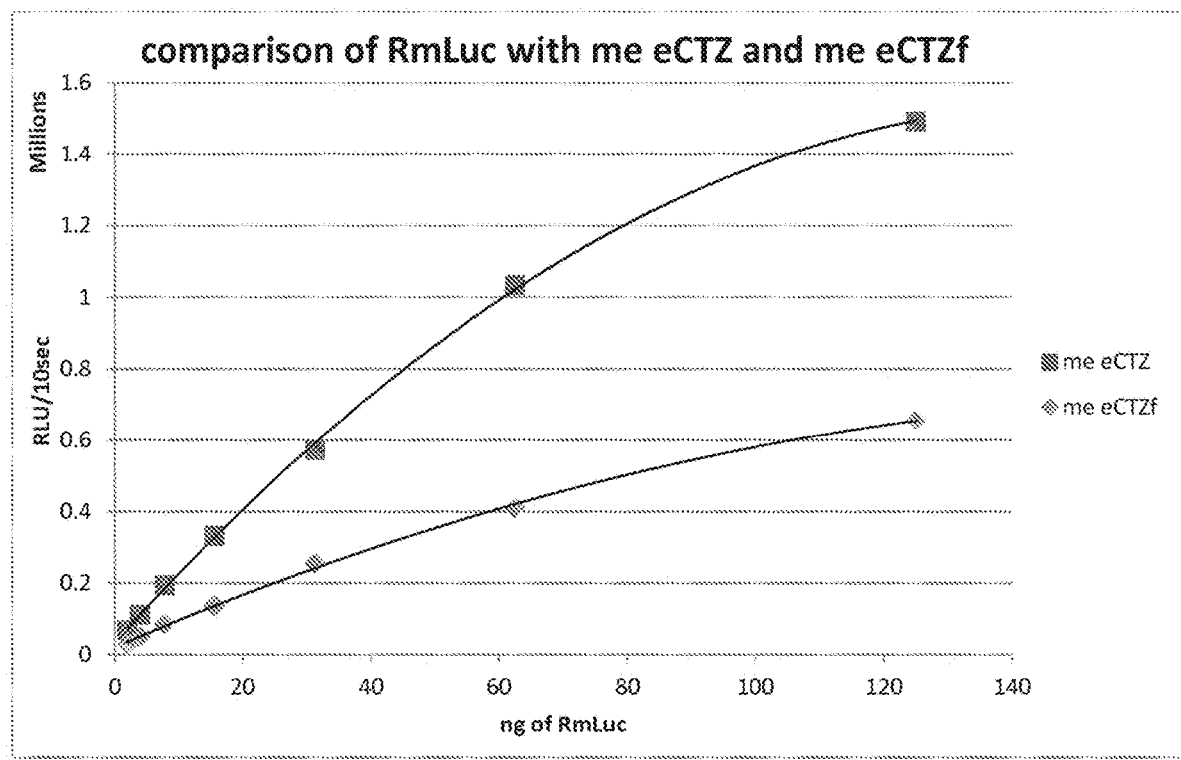
FIG. 21 is luminescent activity of *Renilla muelleri* Luciferase with methoxy eCTZ and methoxy eCTZf. Methoxy eCTZ is showing the same emission spectrum like methoxy eCTZf with *Renilla muelleri* luciferase but has an approx. two-fold higher light-output when integrated over 10 sec.
Figure 22:
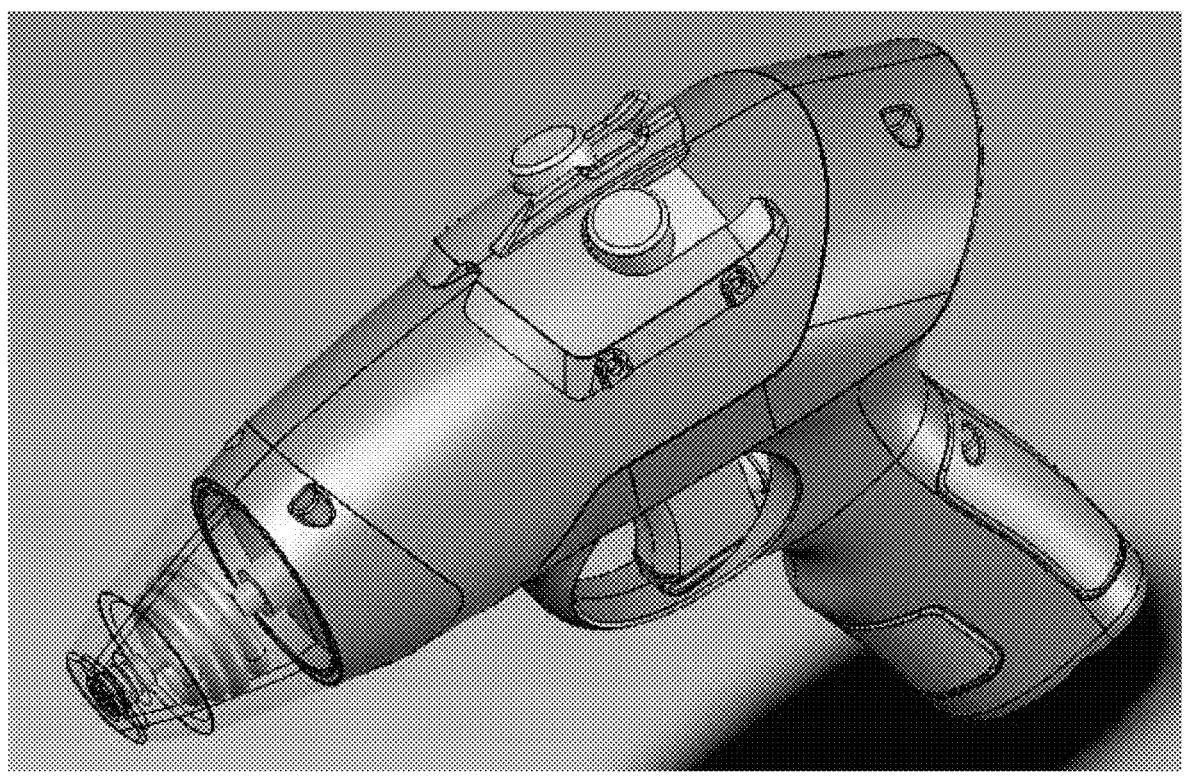
FIG. 22 is the disclosure of the two chambered water gun for delivery of the Coelenterazine or analogues thereof.

As can be immediately realized from inspection of FIG. 13, a selection of colors is obtained using a library of Coelenterazine analogs and known CAP mutations. Many colors, hues, and useful light emitting properties are screened for visually or by optical spectral scanners or color cameras recording the signals for analysis from an array of mixtures to determine which CAP-Coelenterazine analog mixture is ideal.

Example 3

Fluorescent Protein Combined with CAPs to Alter Color

Currently the list of known Fluorescent Proteins is quite large, and many colors are available on the commercial market. These would be selected based upon their known published properties and combined either by making a fusion protein of the Fluorescent Protein to a linker and then combining that with the nucleic acid sequence of the CAP, or using direct synthesis of the new gene and manufacturing the desired CAP-FP fusion protein utilizing recombinant bacteria. Another method is simply freeze-drying a mixed calcium free solution of the CAP with the desired Fluorescent Protein in the correct molar ratios.

Example 4

CARP and CAP Entertainment Applications

When this mixture of CAP and CARP is applied to the audience during a movie, the environmental calcium ions found on the audience person's clothes, skin, hair, will immediately react with the CAP to release a bright shower of light, and simultaneously the CARP releases the Coeleneterazine (or analog) upon absorption of calcium ions too. This makes the Coelenterazine available to the CAP which has already bound calcium locked within its calcium binding domains, causing it to function as a weak "pseudo-luciferase" emitting a low background of light for as long as the un-oxidized Coelenterazine (or analog) is present.

This can be used to create some very interesting effects, because the CARP can be made with a different analog of Coelenterazine and added to the calcium free mixture of CAP and freeze dried together.

Once this mixture is sprayed on the audience, as the CAP initially reacts with calcium ions on the audience it will create bright light corresponding with the Coelenterazine analog it was manufactured with. As the calcium ions are also picked up by calcium on the audience they begin to release their bound different Coelenterazine analog which begin to alter the color of the light produced as the "pseudo-luciferase" starts reacting with the free Coelenterazine (or analog) released nearby from the CARP.

Example 5

CARP and Coelenterazine Utilizing Luciferases

Another embodiment is the use of Coelenterazine Utilizing Luciferases not limited to but for example luciferases such as *Gaussia* Luciferase (native *Coelenterazine*), *Renilla* sp Luciferase (multiple analog use), *Oplophorus* Luciferase, *Pleuromamma* Luciferase, *Periphylla* Luciferase, and mutants that are known or unknown as long as they utilize Coelenterazine or Coelenterazine analogs they are to be known herein as Coelenterazine Utilizing Luciferases (or coelenterazine utilizing luciferases the capitalization is of no consequence for this patent). Suppose the Director of the movie wished to have a prolonged light emission emanating from one portion of the Audience or Stage in a particular color and another brief reaction or "splash' of light emanating from another portion or wall of the theater, stage, or Audience; this can be achieved by manufacture of the combination of a CARP and Coelenterazine Utilizing Luciferase and freeze drying them mixed together in solution.

Just prior to the performance or starting the movie, the mixture is reconstituted with calcium free water, and loaded into the designating ceiling apparatus above the section where the continuous light is desired.

In the other section of the theater, where the brief "splash" of light is desired, the CAP is sprayed on the Audience and a bright flash ensues, while at the other end the calcium activated Coelenterazine releasing protein is becoming active and gradually releasing the Coelenterazine (or analog) to create the longer lasting effect.

The area of the theater that is to release very bright light (the "splash") can have an application of Calcium Chloride ($CaCl_2$) pre-applied and dried so that when the CAP in solution mixes with it in that designated area, a rapid release of light occurs, especially bright if the proper Coelenterazine analog is chosen based upon published characteristics of the analog and CAP.

This disclosure results from an accidental discovery from a splash of CAPs that occurred during manufacture in our laboratory. Some CAP solution landed directly into a lab workers eye. The lab worker went for the bathroom and noticed something glowing from his eye in the mirror. Distracted, he looked into the mirror to find his eye was glowing very brightly with blue light emitting directly from his soft contact lens. Upon hearing of this, the inventor recalled cartoons seen on TV from his youth where the bats in the cave or the monster in the cave had glowing eyes and prompted the thinking to develop this process for theater applications.

Example 6

Glowing Eyes

Another embodiment is the application of CARP and CAP in solution loaded in a eye wash bottle and just before the scene the Actor can use the eyewash and soak the lenses then walk out upon the stage as the lights are off and have glowing eyes.

The color of the light produced for the effect in the eye can be modulated by using a different analog of Coelenterazine during manufacture of the CAP, or a photoprotein mutation as described in the prior examples, or a CARP manufactured with a Coelenterazine analog producing the desired effect.

Example 7

Medical Ophthalmologic Eye Examination

Diagnosis of conjunctiva pathology and corneal scratches and other acute ocular emergencies such as foreign objects is best performed using an ultraviolet lamp and fluorescein dye. However there are situations, such as camping, or in poorer nations where electricity and ultraviolet lamps are not available. Another embodiment of this invention is a kit containing fluorescein dye, and a CARP manufactured using a ultraviolet producing Coelenterazine analog such as 400a or better because it is much brighter, is methoxy-eCoelenterazine analog contained and stabilized within a freeze dried CARP which can be used for eye examinations in the field.

Denuded and scratched corneal surfaces should release more calcium then a sealed intact healthy cornea and a CAP may be used alone or in conjunction with fluorescein dye to reveal the exact location of the foreign body or severity of the ocular corneal scratch. Multiple sets of Coelenterazine applied directly in Rabbit conjunctiva, even at high concentrations, failed to produce any ocular injury.

Example 8

Warm Water and CAPs Leave no Spots on Clothes

This disclosure teaches intentional testing of CAPs in theater situations at home. Test subjects watching a movie were splashed with a CAP solution.

Using warm water of a temperature that when it lands on the audience will not make them feel a cold splash. CAPs in solution should land at skin temperature or slightly warmer to be acceptable to the Audience. CAPS bind absorb calcium from clothes; and does not leave watermarks or marks of any kind on even the finest silks tested, a fortuitous discovery for commercialization.

After binding with calcium CAPS protein release Coelenteramide which is clear to slightly cloudy white in solution but colorless when dry.

Example 9

Fluorescent Protein Mixed with CAPs

Another interesting teaching discovery was made while incorporating fluorescent proteins into CAPs mixtures; unlike most pigments and fluorescent dyes commercially available, Fluorescent Proteins can be chosen that dry perfectly clear and can only be seen under very specific illumination conditions when dry. Fluorescent Proteins can be chosen that do not stain the audience's clothes, but still retaining their fluorescent function when dry.

This has the added benefit that after the Audience that has been splashed in a 3D, 4D, or otherwise average regular movie theater fitted with a simple apparatus for delivering the CAPs, CARP, and/or Fluorescent Protein combination onto the Audience, it will not anger the Audience at the end of the show by staining their clothes.

The CAPS and CARP compositions will be empirically chosen by experimentation to achieve the cinematic effect desired by the Director and also become invisible after drying upon the theater fixtures, and audience while exiting.

Example 10

Theater Egress Entertainment Scare Tactic

Unknown to the Audience at the time, (part of the CAP composition applied during the performance), as the Audience leaves the theater to walk out the exit, the exits are equipped with special light sources designed to excite the dried Fluorescent Proteins on their clothes, hair, and skin and make the Audience think they have been "infected" by the interaction with the movie.

*Renilla* Green Fluorescent Protein (R-GFP) is an excellent vehicle for this effect, it dries clear, and when dry can fluoresce under blue light as the Audience is leaving the theater. It would be possible for the Audience to experience different colors on their clothes in the theater or upon leaving the theater so that some members of the Audience glow in one color and other members of the Audience glow in other colors. This example can also be used for desired effects during the performance or showing of the movie, by equipping the theatre with the light sources of the correct wavelength to excite the applied Fluorescent Proteins.

Apparatus for Equipping the Theater with a CAP and CARP Delivery System.

Theater owners are very cost sensitive to changes made to their theaters. To make a commercially viable venture they have to be willing to modify their theater to accommodate the delivery of CAPS. There are many ways to do this, simple or elaborate; the easiest and least expensive is to simply hang thin walled vinyl tubing over a designated splash zone in the theater (which can be sprayed or dusted prior to performance with calcium chloride). Perforations are made in the tubing over the seats, and the tubing is blown out after each performance because cold water is to be avoided, also drying prevents bacterial growth, CAPs and CARPS are proteins and are suitable growth media for bacteria. The lines will have to be periodically rinsed with an antibacterial agent, such as mild hypochlorite solution, or 70% ethanol.

Prior to the start of the movie, or in advance of the scenes in which the CAPs are to be sprayed, the projectionist has a bottle of pre-weighed out dry CAPs proteins and precise aliquot of hot distilled water. These are mixed, then drawn up into a large 100-200 ml syringe and pushed into the perforated tubing by manually injecting the solution into the tubing system at the appropriate time since the movie, or performance, is tagged by the Director in a way to tell the projectionist or theater personnel to apply the CAP at a selected moment.

More sophisticated devices can be used and installed. Current 4D theaters are already equipped with individual seat sprayers. In this case a mechanical device such as peristaltic, rotary lobe or other pump can be "Y" tube inline mixed and used to spray the CAPs at the Audience. In this case the system must be pre-purged with calcium free water or EDTA solution to remove any calcium on the walls of the tubing. These can be electronically triggered by the movie as it is played, or by signal to the projectionist.

The amount of CAP used is based on the duration and brightness of the effect desired; CAPs store an extremely large amount of light energy in a small weight of protein. The dose range will depend on the quality of the CAPs protein and its storage condition. As little as 0.0001 mg/ml to as much as 1.0 mg/ml is enough to achieve the desired effect.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

Example 11

Coelenterazine Pill

Add 0.1-150 mgs Coelenterazine to 1.0-150 milliliters anhydrous 100% Methanol and warm until completely dissolved, add Polyethylene Glycol, (1,000-10,000 average MW), and warm over steam until all ingredients dissolved and slowly stir in lactose, 20-2,000 milligrams until a paste like consistency is formed, then add Anhydrous Malic Acid, Oxalic, or Citric Acids 1-500 milligrams, and Anhydrous Sodium Bicarbonate at 3-2000 milligrams. Add 1-5% plant butter as binding agent and compress into desired pill form using a standard pilling machine. Adjust compression empirically based on time required to dissolve the pill in water and maintain pill shape for handling and packaging.

Example 12

Luciferase Pill

Luciferase Pill: Mix 1-100 mgs lyophilized *Gaussia*, or *Renilla* Luciferase powder with 100-2,000 milligrams Lactose, 10-100 mgs Microcrystalline cellulose, 5-200 mgs Potassium Bromide, 1-50 milligrams L-Alanine, 1-50 milligrams L-Lysine, 0.1-50 milligrams Stearic acid, 10-200 milligrams Poloxamer, 1-200 milligrams Mango butter and compress into desired pill size and shape. Adjust compression empirically based on time required to dissolve the pill in water and maintain pill shape for handling and packaging.

Luciferase Pill designed for different color of light output: Mix 1-100 mgs lyophilized *Gaussia*, or *Renilla* Luciferase powder with 2-300 milligrams of Lyophilized Fluorescent Protein, 100-2,000 milligrams Lactose, 10-100 mgs Microcrystalline cellulose, 5-200 mgs Potassium Bromide, 1-50 milligrams L-Alanine, 1-50 milligrams L-Lysine, 0.1-50 milligrams Stearic acid, 10-200 milligrams Poloxamer, 1-200 milligrams Mango butter and compress into desired pill size and shape. Adjust compression empirically based on time required to dissolve the pill in water and maintain pill shape for handling and packaging.

Example 13

Kit for the Water Soluble Coelenterazine

A kit containing a reagent that contains a buffer for the Coelenterazine (Buffer A) and for the *Gaussia* luciferase (Buffer B).

The kit may further include Vitamin C (25-30 uM) together with Coelenterazine and the solubilizing polymer. Everything will be dissolved and then dried to a powder to prolong shelf-life. Buffer A is mixed to this Coelenterazine containing powder. The buffer itself will not contain any Vit. C only after it is mixed with the dried Coelenterazine. Further containing KI (Potassium Iodine) which reduces the background luminescence. in Buffer B as approximately 50 mM concentration. This Buffer contains no Coelenterazine. It will only come in contact with the Coelenterazine in the luminometer. The final Coelenterazine concentration will be between 10-100 uM. The concentration may be 50 uM.

The above examples include the use of Coelenterazine or analogs as described herein.

The description of the present invention has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiment described and shown in the figures was chosen and described in order to best explain the principles of the invention, the practical application, and to enable others of ordinary skill in the art to understand the invention for various embodiments with various modifications as are suited to the particular use contemplated.

What is claimed is:

1. A method for visually enhancing the experience of an audience during a performance, wherein the method comprises:

(a) contacting a composition comprising an aqueous composition comprising a calcium activated photoprotein with a calcium containing surface of the audience; or (b) directly applying a composition comprising an aqueous composition comprising a calcium activated photoprotein to a calcium containing surface containing the audience;

wherein the performance is selected from the group consisting of a cinematic performance, a music performance, a stage performance, and a theatrical performance;

wherein the calcium containing surface of the audience is selected from the group consisting of the clothing of a person, the hair of a person, and the skin of a person;

wherein the calcium containing surface containing the audience is selected from the group consisting of a chair and a floor;

wherein the calcium activated photoprotein is a natural or semi-synthetic calcium activated photoprotein derived from aequorin; and wherein the aqueous composition comprising a calcium activated photoprotein comprises a natural or semi-synthetic calcium activated photoprotein derived from aequorin that is bound to a compound selected from the group consisting of:

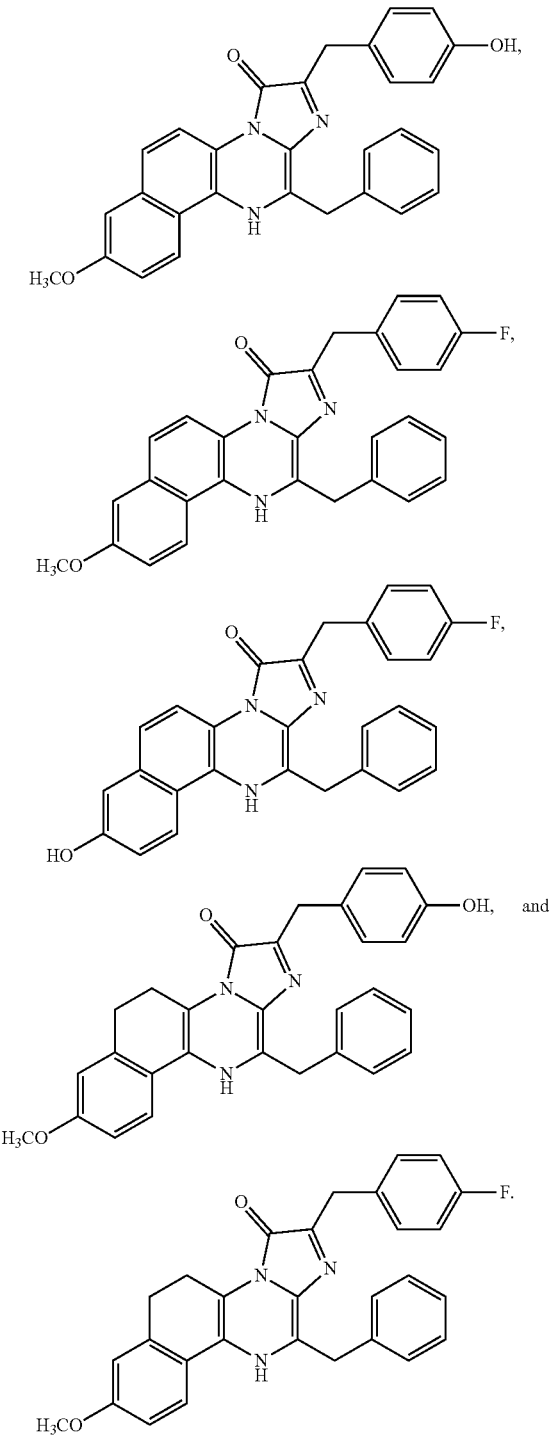

2. The method of claim 1, wherein the composition comprising the aqueous composition comprising the natural or semi-synthetic calcium activated photoprotein derived from aequorin is a solution.

3. The method of claim 2, wherein the aqueous composition comprising the natural or semi-synthetic calcium activated photoprotein derived from aequorin further comprises a buffer selected from the group consisting of purified water free of calcium and magnesium cations, distilled water of neutral pH, a 0.0001-0.1 molar ethylene glycol tetraacetic acid solution, and a 0.0001-0.1 molar ethylenediaminetetraacetic acid solution.

4. The method of claim 3, wherein the aqueous composition comprising the natural or semi-synthetic calcium activated photoprotein derived from aequorin further comprises purified water free of calcium and magnesium cations.

5. The method of claim 1, wherein the composition comprising the aqueous composition comprising the natural or semi-synthetic calcium activated photoprotein derived from aequorin is a suspension.

6. The method of claim 5, wherein the aqueous composition comprising the natural or semi-synthetic calcium activated photoprotein derived from aequorin further comprises a buffer selected from the group consisting of purified water free of calcium and magnesium cations, distilled water of neutral pH, a 0.0001-0.1 molar ethylene glycol tetraacetic acid solution, and a 0.0001-0.1 molar ethylenediaminetetraacetic acid solution.

7. The method of claim 6, wherein the aqueous composition comprising the natural or semi-synthetic calcium activated photoprotein derived from aequorin further comprises purified water free of calcium and magnesium cations.

8. The method of claim 1, wherein the aqueous composition comprising a natural or semi-synthetic calcium activated photoprotein comprises a semi-synthetic calcium activated photoprotein derived from aequorin.

9. The method of claim 1, wherein the composition comprising an aqueous composition comprising the natural or semi-synthetic calcium activated photoprotein is microencapsulated.

10. The method of claim 1, wherein the composition comprising an aqueous composition comprising the natural or semi-synthetic calcium activated photoprotein further comprises a fluorescent protein, dye, or quantum dot.

11. The method of claim 1, wherein contacting the composition comprising an aqueous composition comprising the natural or semi-synthetic calcium activated photoprotein derived from aequorin with the calcium containing surface of the audience:
(a) releases the bound compound from the natural or semi-synthetic calcium activated photoprotein derived from aequorin; and
(b) produces light visible to the dark adapted human eye.

12. The method of claim 11, wherein further release of the bound compound from the natural or semi-synthetic calcium activated photoprotein derived from aequorin regenerates or prolongs the production of light visible to the dark adapted human eye.

13. The method of claim 1, wherein directly applying the composition comprising an aqueous composition comprising the natural or semi-synthetic calcium activated photoprotein derived from aequorin to the calcium containing surface containing the audience:
(a) releases the bound compound from the natural or semi-synthetic calcium activated photoprotein derived from aequorin; and
(b) produces light visible to the dark adapted human eye.

14. The method of claim 13, wherein further release of the bound compound from the natural or semi-synthetic calcium activated photoprotein derived from aequorin regenerates or prolongs the production of light visible to the dark adapted human eye.

15. The method of claim 1, wherein:
(a) the calcium containing surface of the audience is selected from the group consisting of the hair of a person and the skin of a person; or
(b) the calcium containing surface containing the audience is a chair.

16. The method of claim 1, wherein the natural or semi-synthetic calcium activated photoprotein derived from aequorin is bound to a compound selected from the group consisting of:

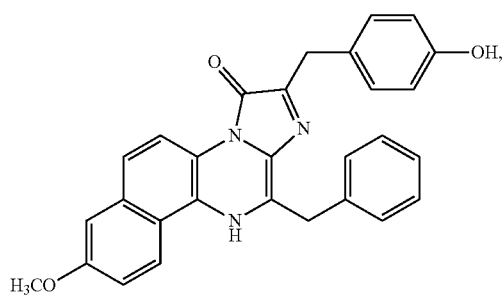

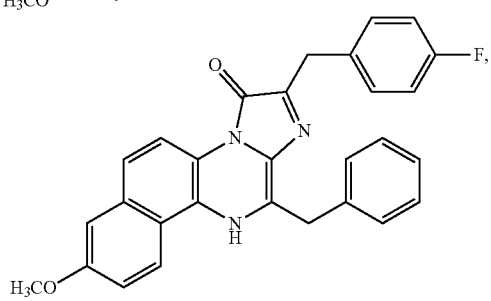

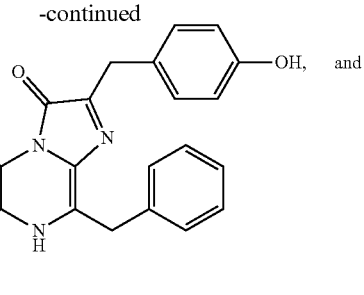

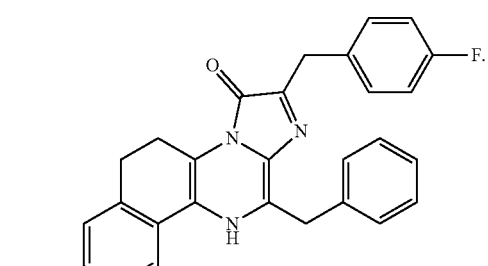

* * * * *